United States Patent
Connell et al.

[11] Patent Number: 5,714,494
[45] Date of Patent: Feb. 3, 1998

[54] XANTHINES IN THE 7TH POSITION WITH A BENZYL ACETIC ACID MOIETY

[75] Inventors: Richard Connell, Trumbull, Conn.; Siegfried Goldmann; Ulrich Müller, both of Wuppertal, Germany; Stefan Lohmer, Milan, Italy; Hilmar Bischoff; Dirk Denzer, both of Wuppertal, Germany; Rudi Grützmann, Solingen, Germany; Stefan Wohlfeil, Hilden, Germany

[73] Assignee: Bayer Aktiengesellschaft, Leverkusen, Germany

[21] Appl. No.: 710,503

[22] Filed: Sep. 18, 1996

[30] Foreign Application Priority Data

Sep. 25, 1995 [DE] Germany ............... 195 35 504.0

[51] Int. Cl.⁶ .................. A61K 31/52; C07D 473/08; C07D 473/22; C07D 473/06
[52] U.S. Cl. .................. 514/263; 544/268; 544/269; 544/270; 544/271
[58] Field of Search .................. 514/263; 544/271, 544/268, 269, 270

[56] References Cited

U.S. PATENT DOCUMENTS

| | | | |
|---|---|---|---|
| 4,061,753 | 12/1977 | Bodor | 544/271 |
| 5,352,687 | 10/1994 | Müller et al. | 514/341 |
| 5,420,149 | 5/1995 | Müller et al. | 514/399 |
| 5,521,206 | 5/1996 | Müller et al. | 546/278 |
| 5,527,809 | 6/1996 | Müller-Gliemann et al. | 514/303 |

FOREIGN PATENT DOCUMENTS

| | | |
|---|---|---|
| 0 363 320 A3 | 4/1990 | European Pat. Off. |
| 42 00 954 A1 | 10/1992 | Germany |
| 2 276 383 | 9/1994 | United Kingdom |

OTHER PUBLICATIONS

F. Carey, "Organic Chemistry" (2nd Edition), p. 1217 (1992).

Primary Examiner—Mark L. Berch
Attorney, Agent, or Firm—Sprung Kramer Schaefer & Briscoe

[57] ABSTRACT

Substituted xanthines of formula

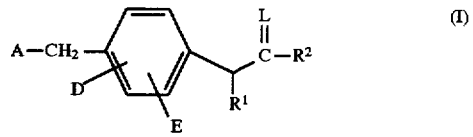

in which A represents a radical of the formula

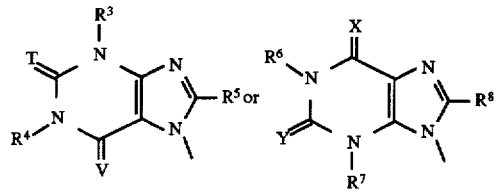

in which $R^3$, $R^4$, $R^6$ and $R^7$ denote hydrogen, cycloalkyl, aryl having 6 to 10 carbon atoms, or denote straight-chain of branched alkyl or alkenyl, each of which is optionally substituted; T, V, X and Y are identical or different and denote an oxygen or sulphur atom; $R^5$ and $R^8$ are identical or different and denote hydrogen, halogen, cycloalkyl having 3 to 8 carbon atoms or straight-chain or branched alkyl or alkenyl in each case having up to 8 carbon atoms, optionally substituted or $R^5$ and $R^8$ denote aryl having 6 to 10 carbon atoms or a 5- to 7-membered aromatic, optionally benzo-fused heterocycle having up to 3 heteroatoms S, N and/or O, each of which is optionally substituted; L represents an oxygen or sulphur atom; $R^2$ represents mercapto, hydroxyl, straight-chain or branched alkoxy having up to 8 carbon atoms or the group of the formula

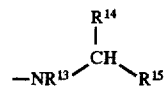

in which $R^{13}$ denotes hydrogen or straight-chain or branched alkyl having up to 4 carbon atoms; $R^{14}$ denotes hydrogen, phenyl or a 5- to 6-membered aromatic heterocycle having up to 3 heteroatoms S, N and/or O; and $R^{15}$ denotes hydrogen or straight-chain or branched alkyl having up to 8 carbon atom, optionally substituted by hydroxyl, and their salts are prepared by reaction of the suitable unsubstituted xanthines with halogenomethylphenylacetic acids and subsequent reaction of the carboxylic esters or acids with phenylglycinolamine. The substituted xanthines are suitable as active compounds in medicaments, in particular in antiatherosclerotic medicaments.

11 Claims, No Drawings

XANTHINES IN THE 7TH POSITION WITH A BENZYL ACETIC ACID MOIETY

The present invention relates to substituted xanthines, processes for their preparation and their use as medicaments, in particular as antiatherosclerotic medicaments.

It is known that raised blood levels of triglycerides (hypertriglyceridaemia) and cholesterol (hypercholesterolaemia) are associated with the genesis of atherosclerotic vascular wall changes and coronary heart diseases.

A distinctly increased risk of the development of coronary heart disorders is moreover present if these two risk factors occur in combination, accompanied, in turn, by an overproduction of apolipoprotein E-100. There is therefore still a great need to make available medicaments for the control of atherosclerosis and coronary heart diseases.

The present invention relates to substituted xanthines of the general formula (I)

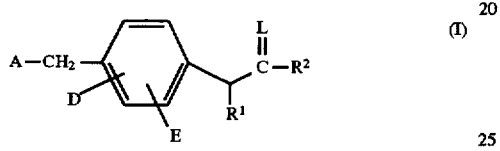

in which

A represents a radical of the formula

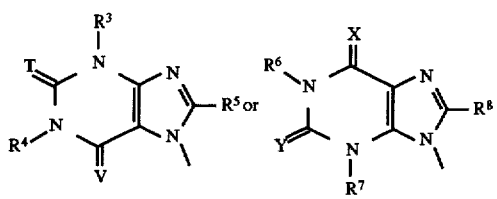

in which
- $R^3$, $R^4$, $R^6$ and $R^7$ are identical or different and denote hydrogen, cycloalkyl having 3 to 7 carbon atoms or aryl having 6 to 10 carbon atoms,
  or denote straight-chain branched alkyl or alkenyl in each case having up to 8 carbon atoms, each of which is optionally substituted by halogen, hydroxyl or aryl having 6 to 10 carbon atoms,
- T, V, X and Y are identical or different and denote an oxygen or sulphur atom,
- $R^5$ and $R^8$ are identical or different and denote hydrogen, halogen, cycloalkyl having 3 to 8 carbon atoms or straight-chain or branched alkyl or alkenyl in each case having up to 8 carbon atoms, each of which is optionally substituted by cycloalkyl having 3 to 8 carbon atoms, or by a 5- to 6-membered, aromatic, optionally benzo-fused heterocycle having up to 3 heteroatoms from the series X, N and/or O, by aryl having 6 to 10 carbon atoms, where the cycles for their part can be substituted identically or differently up to 3 times by a 5- to 6-membered aromatic heterocycle having up to 3 heteroatoms from the series S, N and/or O, or by phenyl, benzyl, halogen, hydroxyl, carboxyl or straight-chain or branched alkyl, alkoxy or alkoxycarbonyl in each case having up to 6 carbon atoms, or denote aryl having 6 to 10 carbon atoms or a 5- to 7-membered aromatic, optionally benzo-fused heterocycle having up to 3 heteroatoms from the series S, N and/or O, each of which is optionally substituted identically or differently up to 3 times by halogen, phenyl, trifluoromethyl, hydroxy, carboxyl or straight-chain or branched alkyl, alkoxy or alkoxycarbonyl in each case having up to 6 carbon atoms or by a group of the formula $-(CO)_a-NR^9R^{10}$, in which
  a denotes a number 0 or 1,
  $R^9$ and $R^{10}$ are identical or different and denote hydrogen, phenyl or straight-chain or branched alkyl or acyl in each case having up to 5 carbon atoms,
- D and E are identical or different and represent hydrogen, halogen, trifluoromethyl, hydroxyl, carboxyl or straight-chain or branched alkyl, alkoxy or alkoxycarbonyl in each case having up to 6 carbon atoms,
- $R^1$ represents hydrogen or cycloalkyl having 3 to 8 carbon atoms, or represents straight-chain or branched alkyl or alkenyl in each case having up to 8 carbon atoms, each of which is optionally substituted by cycloalkyl having 3 to 6 carbon atoms, phenyl or a 5- to 6-membered aromatic heterocycle having up to 3 heteroatoms from the series S, N and/or O, or
  represents phenyl or a 5- to 6-membered aromatic heterocycle having up to 3 heteroatoms from the series S, N and/or O, where the ring systems are optionally substituted identically or differently up to 3 times by halogen, phenyl, trifluoromethyl or straight-chain or branched alkyl or alkoxy in each case having up to 5 carbon atoms, hydroxyl or a group of the formula $-NR^{11}R^{12}$, in which
  $R^{11}$ and $R^{12}$ have the meaning of $R^9$ and $R^{10}$ given above and are identical to or different from this,
- L represents an oxygen or sulphur atom,
- $R^2$ represents mercapto, hydroxyl, straight-chain or branched alkoxy having up to 8 carbon atoms or the group of the formula

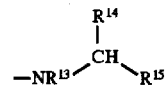

in which
- $R^{13}$ denotes hydrogen or straight-chain or branched alkyl having up to 4 carbon atoms,
- $R^{14}$ denotes hydrogen, phenyl or a 5- to 6-membered aromatic heterocycle having up to 3 heteroatoms from the series S, N and/or O,
- $R^{15}$ denotes hydrogen or straight-chain or branched alkyl having up to 8 carbon atoms, which is optionally substituted by hydroxyl, and their salts.

The substituted xanthines according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention, which have a free carboxyl group. Those particularly preferred are, for example, sodium, potassium, magnesium or calcium salts, and also ammonium salts which are derived from ammonia, or organic amines, for example ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as image and mirror image (enantiomers), or which do not behave as image and mirror image (diastereomers). The invention relates both to the enantiomers or diastereomers and to their respective mixtures. These mixtures of the enantiomers and diastereomers can be separated into the stereoisomerically uniform constituents in a known manner.

Heterocycle, if appropriate benzo-fused, in the context of the invention in general represents a saturated or unsaturated 5- to 7-membered, preferably 5- to 6-membered, heterocycle which can contain up to 3 heteroatoms from the series S, N and/or O. Examples which may be mentioned are: indolyl, quinolyl, benzo[b]thiophene, benzo[b]furanyl, pyridyl, thienyl, furyl, pyrrolyl, thiazolyl, oxazolyl, imidazolyl, morpholinyl or piperidyl. Quinolyl, furyl, pyridyl and thienyl are preferred.

Preferred compounds of the general formula (I) are those in which

A represents a radical of the formula

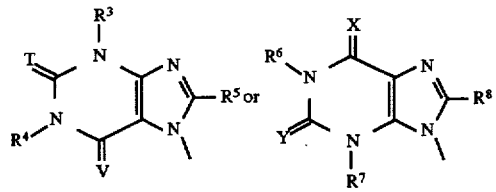

in which

R$^3$, R$^4$, R$^6$ and R$^7$ are identical or different and denote hydrogen, phenyl, cyclopropyl, cyclopentyl or cyclohexyl, or denote straight-chain or branched alkyl or alkenyl in each case having up to 6 carbon atoms, each of which is optionally substituted by fluorine, chlorine, bromine, hydroxyl or phenyl, T, V, X and Y are identical or different and denote an oxygen or sulphur atom, R$^5$ and R$^8$ are identical or different and denote hydrogen, fluorine, chlorine, bromine, cyclopropyl, cyclobutyl, cyclopentyl, cyclohexyl, cycloheptyl or straight-chain or branched alkyl or alkenyl in each case having up to 6 carbon atoms, each of which is optionally substituted by cyclopropyl, cyclopentyl, cyclohexyl, cycloheptyl, naphthyl, phenyl, pyridyl, thienyl or furyl, which for their part can be substituted identically or differently up to 2 times by phenyl, benzyl, fluorine, chlorine, bromine, hydroxyl or straight or branched alkyl or alkoxy in each case having up to 4 carbon atoms, or denote phenyl, pyridyl, thienyl or furyl, each of which is optionally substituted identically or differently up to 2 times by fluorine, chlorine, bromine, phenyl, trifluoromethyl, hydroxyl or straight-chain or branched alkyl or alkoxy in each case having up to 4 carbon atoms or a group of the formula —(CO)$_a$—NR$^9$R$^{10}$, in which a denotes a number 0 or 1, R$^9$ and R$^{10}$ are identical or different and denote hydrogen, phenyl or straight-chain or branched alkyl or acyl in each case having up to 4 carbon atoms, D and E are identical or different and represent hydrogen, fluorine, chlorine, bromine, trifluoromethyl, hydroxyl or straight-chain or branched alkyl or alkoxy in each case having up to 4 carbon atoms, R$^1$ represents hydrogen, cyclopropyl, cyclobutyl, cyclopentyl, cyclohexyl, cycloheptyl or straight-chain or branched alkyl or alkenyl in each case having up to 6 carbon atoms, each of which is optionally substituted by cyclopropyl, cyclopentyl, cyclohexyl, phenyl, pyridyl or thienyl, or represents phenyl, pyridyl, furyl or thienyl, each of which is optionally substituted identically or differently up to 2 times by fluorine, chlorine, bromine, phenyl, trifluoromethyl or straight-chain or branched alkyl or alkoxy in each case having up to 4 carbon atoms or a group of the formula —NR$^{11}$R$^{12}$, in which R$^{11}$ and R$^{12}$ have the meaning of R$^9$ and R$^{10}$ given above and are identical to or different from this, L represents an oxygen or sulphur atom, R$^2$ represents mercapto, hydroxyl, straight-chain or branched alkoxy having up to 6 carbon atoms or the group of the formula

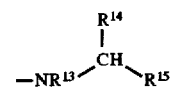

in which

R$^{13}$ denotes hydrogen or straight-chain or branched alkyl having up to 4 carbon atoms, R$^{14}$ denotes hydrogen, phenyl, pyridyl, furyl or thienyl, R$^{15}$ denotes hydrogen or straight-chain or branched alkyl having up to 6 carbon atoms, which is optionally substituted by hydroxyl, and their salts.

Particularly preferred compounds of the general (I) are those in which

A represents a radical of the formula

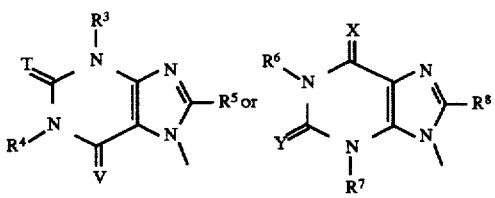

in which

R$^3$, R$^4$, R$^6$ and R$^7$ are identical or different and denote hydrogen, phenyl, cyclopropyl, cyclopentyl or cyclohexyl, or denote straight-chain or branched alkyl or alkenyl in each case having up to 5 carbon atoms, each of which is optionally substituted by fluorine, chlorine, bromine, hydroxyl or phenyl, T, V, X and Y are identical or different and denote an oxygen or sulphur atom, R$^5$ and R$^8$ are identical or different and denote hydrogen, fluorine, chlorine, bromine, cyclopropyl, cyclobutyl, cyclopentyl, cyclohexyl, cycloheptyl or straight-chain or branched alkyl or alkenyl in each case having up to 5 carbon atoms, each of which is optionally substituted by cyclopropyl, cyclopentyl, cyclohexyl, cycloheptyl, phenyl, pyridyl, thienyl or furyl, which for their part can be substituted identically or differently up to 2 times by phenyl, benzyl, fluorine, chlorine, bromine, hydroxyl or straight-chain or branched alkyl or alkoxy in each case having up to 3 carbon atoms, or denote phenyl, pyridyl, thienyl or furyl, each of which is optionally substituted identically or differently up to 2 times by fluorine, chlorine, bromine, phenyl, trifluoromethyl, hydroxyl or straight-chain or branched alkyl or alkoxy in each case having up to 3 carbon atoms or a group of the formula —(CO)$_a$—NR$^9$R$^{10}$, in which a denotes a number 0 or 1, R$^9$ and R$^{10}$ are identical or different and denote hydrogen, phenyl or straight-chain or branched alkyl or acyl in each case having up to 3 carbon atoms, D and E are identical or different and represent hydrogen, fluorine, chlorine, bromine or trifluoromethyl, R$^1$ represents hydrogen, cyclopropyl, cyclobutyl, cyclopentyl, cyclohexyl, cycloheptyl or straight-chain or branched alkyl or alkenyl in each case having up to 5 carbon atoms, each of which is optionally substituted by cyclopropyl, cyclopentyl, cyclohexyl, phenyl, pyridyl or thienyl, or represents phenyl, pyridyl, furyl or thienyl, each of which is optionally substituted identically or differently up to 2 times by fluorine, chlorine, bromine, phenyl, trifluoromethyl or straight-chain or branched alkyl or alkoxy in each case having up to 3 carbon atoms or a group of the formula —NR$^{11}$R$^{12}$, in which R$^{11}$ and R$^{12}$ have the meaning of R$^9$ and R$^{10}$ given above and are identical to or different from this, L represents an oxygen or sulphur atom, R$^2$ represents mercapto, hydroxyl, straight-chain or branched alkoxy having up to 5 carbon atoms or the group of the formula

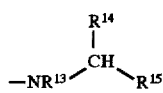

in which

R$^{13}$ denotes hydrogen or straight-chain or branched alkyl having up to 3 carbon atoms, R$^{14}$ denotes hydrogen, phenyl, pyridyl or thienyl, R$^{15}$ denotes hydrogen or straight-chain or branched alkyl having up to 3 carbon atoms, which is optionally substituted by hydroxyl, and their salts.

Very particularly preferred compounds of the general formula (I) are those in which A represents a radical of the formula

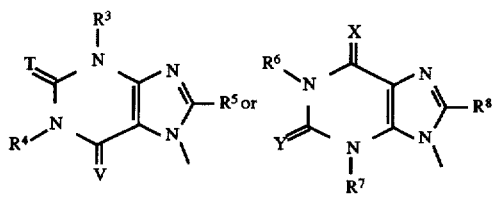

in which

R$^3$, R$^4$, R$^6$ and R$^7$ are hydrogen, straight-chain or branched alkyl in each case having up to 4 carbon atoms, T, V, X and Y are identical or different and denote an oxygen or sulphur atom, R$^5$ and R$^8$ are identical or different and denote hydrogen, fluorine, chlorine, bromine, cyclopropyl, cyclopentyl, cyclohexyl or straight-chain or branched alkyl or alkenyl in each case having up to 3 carbon atoms, each of which is optionally substituted by cyclopropyl, cyclopentyl, cyclohexyl, phenyl, pyridyl, thienyl or furyl, which for their part can be substituted identically or differently up to 2 times by phenyl, benzyl, fluorine, chlorine, bromine, hydroxyl or straight-chain or branched alkyl or alkoxy in each case having up to 3 carbon atoms, or denote phenyl, pyridyl, thienyl or furyl, each of which is optionally substituted identically or differently up to 2 times by fluorine, chlorine, bromine, phenyl, trifluoromethyl, hydroxyl or straight-chain or branched alkyl or alkoxy in each case having up to 3 carbon atoms or a group of the formula —(CO)$_a$—NR$^9$R$^{10}$, in which a denotes the number 0, R$^9$ and R$^{10}$ are identical or different and denote hydrogen or straight-chain or branched alkyl in each case having up to 3 carbon atoms, D and E are identical or different and represent hydrogen, fluorine, chlorine, bromine or trifluoromethyl, R$^1$ represents hydrogen, cyclopropyl, cyclopentyl, cyclohexyl, cycloheptyl, phenyl or straight-chain or branched alkyl having up to 5 carbon atoms, L represents an oxygen atom, R$^2$ represents hydroxyl, straight-chain or branched alkoxy having up to 5 carbon atoms or the group of the formula

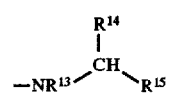

in which

R$^{13}$ denotes hydrogen or straight-chain or branched alkyl having up to 3 carbon atoms, R$^{14}$ denotes phenyl, R$^{15}$ denotes straight-chain or branched alkyl having up to 3 carbon atoms, which is optionally substituted by hydroxyl, and their salts.

A process for the preparation of the compounds of the general formula (I) according to the invention has additionally been found, characterized in that first, by reaction of compounds of the general formula (II)

A—H           (II)

in which

A has the meaning given above, with compounds of the general formula (III)

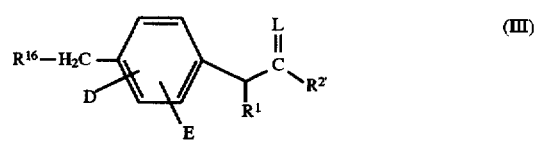

in which

D, E, L and R$^1$ have the meaning given above,

R$^{16}$ represents hydroxyl or halogen, preferably bromine, and

R$^{2'}$ represents straight-chain or branched alkoxy having up to 8 carbon atoms, in inert solvents and in the presence of bases and/or auxiliaries, the latter are converted into compounds of the general formula (Ia)

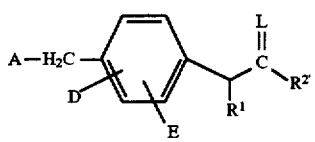

(Ia)

in which

A, D, E, L, R¹ and R²' have the meaning given above, and these are optionally hydrolysed (R²¹OH), or, if appropriate, these acids are reacted with glycinols and glycinol derivatives of the general formula (IV)

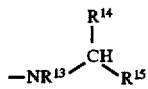

(IV)

in which $R^{13}$, $R^{14}$ and $R^{15}$ have the meaning given above, in inert solvents, if appropriate in the presence of bases and/or auxiliaries.

The process according to the invention can be illustrated by way of example by the following reaction scheme:

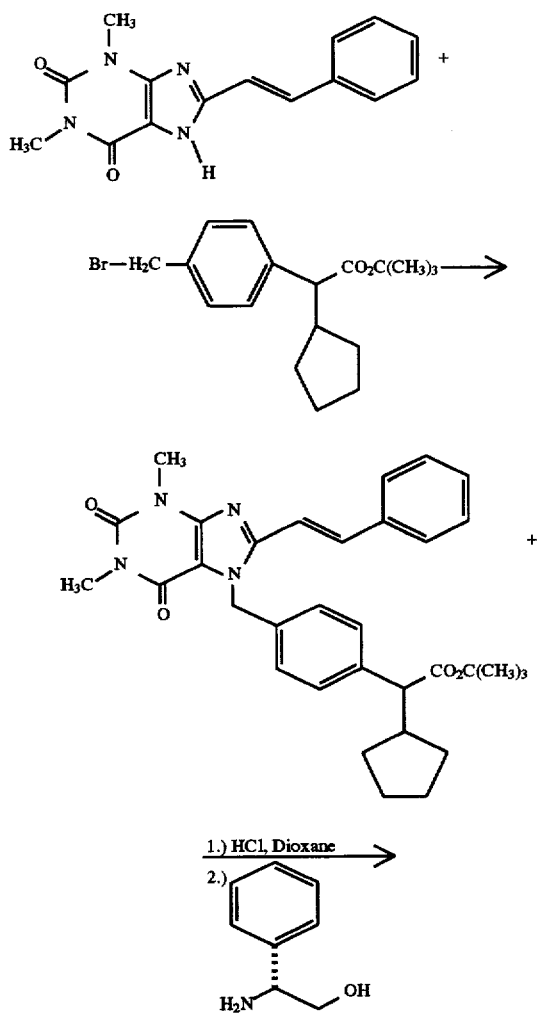

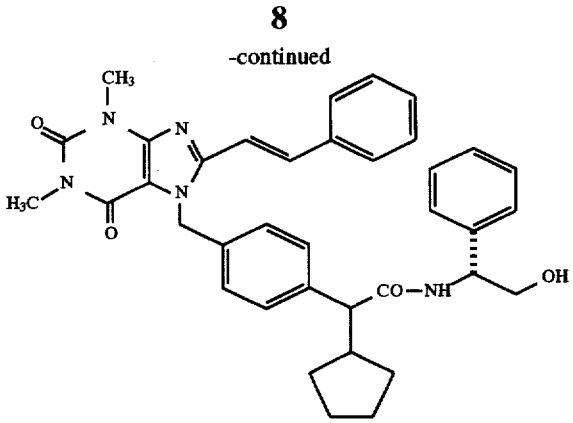

Suitable solvents for the process are customary organic solvents which do not change under the reaction conditions. These preferably include ethers such as diethyl ether, dioxane, tetrahydrofuran, glycol dimethyl ether, or alcohols, for example methanol, ethanol, propanol, isopropanol, butanol, iso-butanol or tert-butanol, or hydrocarbons such as benzene, toluene, xylene, hexane, cyclohexane or petroleum fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Dimethylformamide and tetrahydrofuran are preferred.

Bases which can be employed for the process are in general inorganic or organic bases. These preferably include alkali metal hydroxides, for example sodium hydroxide or potassium hydroxide, alkaline earth metal hydroxides, for example barium hydroxide, alkali metal carbonates such as sodium carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)-amines) such as triethylamine, or heterocycles such as 1,4-diazabicyclo[2.2.2]octane (DABCO), 1,8-diazabicyclo[5.4.0]undec-7-ene(DBU), pyridine, diaminopyridine, methylpiperidine or morpholine. It is also possible to employ as bases alkali metals such as sodium or their hydrides such as sodium hydride. Sodium hydride, potassium carbonate, triethylamine, pyridine and potassium tert-butoxide, DBU or DABCO are preferred.

In general, the base is employed in an amount from 0.05 to 10 mol, preferably from 1 to 2 mol, relative to 1 mol of the compound of the formula (II).

The processes according to the invention are in general carried out in a temperature range from –30° C. to +100° C., preferably from –10° C. to +60° C.

The processes according to the invention are in general carried out at normal pressure. However, it is also possible to carry out the processes at elevated pressure or at reduced pressure (e.g. in a range of from 0.5 to 5 bar).

The carboxylic acid esters are hydrolysed according to customary methods, by treating the esters with customary bases in inert solvents.

Suitable bases for the hydrolysis are the customary inorganic bases. These preferably include alkali metal hydroxides or alkaline earth metal hydroxides, for example sodium hydroxide, potassium hydroxide or barium hydroxide, or alkali metal carbonates such as sodium or potassium carbonate or sodium hydrogen carbonate. Sodium hydroxide or potassium hydroxide or particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis can also be carried out using acids, for example trifluoroacetic acid, acetic acid, hydrochloric acid, hydrobromic acid, methanesulphonic acid, sulphuric acid or perchloric acid, preferably using trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (e.g. from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

Suitable solvents for the reaction with glycinols in this case are inert organic solvents which do not change under the reaction conditions. These preferably include ethers, such as diethyl ether or tetrahydrofuran, halogenohydrocarbons such as dichloromethane, trichloromethane, tetrachloromethane, 1,2-dichloroethane, trichloroethane, tetrachloroethane, 1,2-dichloroethylene or trichloroethylene, hydrocarbons such as benzene, xylene, toluene, hexane, cyclohexane or petroleum fractions, nitromethane, dimethylformamide, acetone, acetonitrile or hexamethylphosphoramide. It is also possible to employ mixtures of the solvents. Dichloromethane, tetrahydrofuran, acetone or dimethylformamide is particularly preferred.

Bases which can be employed here are in general inorganic or organic bases. These preferably include alkali metal hydroxides, for example sodium hydroxide or potassium hydroxide, alkaline earth metal hydroxides, for example barium hydroxide, alkali metal carbonates such as sodium carbonate or potassium carbonate, alkaline earth metal carbonates such as calcium carbonate, or alkali metal or alkaline earth metal alkoxides such as sodium or potassium methoxide, sodium or potassium ethoxide or potassium tert-butoxide, or organic amines (trialkyl($C_1$–$C_6$)amines) such as triethylamine, or heterocycles such as 1,4-diazabicyclo[2.2.2]octane (DABCO), 1,8-diaza-bicyclo[5.4.0]undec-7-ene (DBU), pyridine, diaminopyridine, methylpiperidine or morpholine. It is also possible to employ as bases alkali metals such as sodium and their hydrides such as sodium hydride. Sodium and potassium carbonate and triethylamine are preferred.

The base is employed in an amount from 1 mol to 5 mol, preferably from 1 mol to 3 mol, relative to 1 mol of the appropriate carboxylic acid.

The reaction is in general carried out in a temperature range from 0° C. to 150° C., preferably from +20° C. to +110° C.

The reaction can be carried out at normal, elevated or reduced pressure (e.g. from 0.5 to 5 bar). In general, it is carried out at normal pressure.

The reaction with phenylglycinols can, if appropriate, also proceed via the activated stage of the acid halides, which can be prepared from the corresponding acids by reaction with thionyl chloride, phosphorus trichloride, phosphorus pentachloride, phosphorus tribromide or oxalyl chloride.

The abovementioned bases can, if appropriate, also be employed as acid-binding auxiliaries.

Suitable auxiliaries are also dehydrating reagents. These include, for example, carbodiimides such as diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or iso-butyl chloroformate or benzotriazolyloxy-tris-(dimethylamino)phosphonium hexafluorophosphate or diphenyl phosphoramidate or methane-sulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount from 0.5 to 3 mol, preferably from 1 to 1.5 mol, relative to 1 mol of the corresponding carboxylic acids.

The compounds of the general formulae (III) and (IV) are known per se or can be prepared by customary methods.

The compounds of the general formula (II) are known or can be prepared by reacting, for example, the corresponding 1,3-substituted uracils with orthoformic acid esters or carbonyl chlorides and with aldehydes of the general formula (V)

in which $R^{17}$ includes the meanings of $R^5$ and/or $R^8$ given above, in inert solvents and in the presence of a base.

Suitable solvents for the preparation are the abovementioned solvents. Ethanol, dichloromethane or dimethylformamide is preferred.

The reactions are carried out in a temperature range from 30° C. to 160° C., preferably at the boiling point of the respective solvent and normal pressure.

The aldehydes of the general formula (V) are known per se or can be prepared by customary methods.

The compounds of the general formula (Ia) are new and can be prepared by the process described above.

The compounds of the general formulae (I) and (Ia) according to the invention have an unforeseeable spectrum of pharmacological action.

They can be used as active compounds in medicaments for the reduction of changes to vascular walls and for the treatment of coronary heart disorders, cardiac insufficiency, brain function disorders, ischaemic brain disorders, apoplexy, circulatory disorders, microcirculation disorders and thromboses.

The proliferation of smooth muscle cells furthermore plays a decisive part in the occlusion of vessels. The compounds according to the invention are suitable for inhibiting this proliferation and thus for preventing atherosclerotic processes.

The compounds according to the invention are distinguished by a lowering of ApoB-100-associated lipoproteins (VLDL and its degradation products, e.g. LDL), of ApoB-100, of triglycerides and of cholesterol. They thus have valuable and superior pharmacological properties in comparison with the prior art.

The action of the compounds according to the invention surprisingly consists first in a reduction or complete inhibition of the formation and/or of the release of ApoB-100-associated lipoproteins from liver cells, which results in a lowering of the VLDL plasma level. This VLDL-lowering must be accompanied by a lowering of the plasma levels of ApoB-100, LDL, triglycerides and of cholesterol; thus several of the abovementioned risk factors which are involved in vascular wall changes are simultaneously lowered.

The compounds according to the invention can therefore be employed for the prevention and treatment of atherosclerosis, obesity, pancreatitis and constipation.

1. INHIBITION OF THE RELEASE OF APOB-100-ASSOCIATED LIPOPROTEINS

The test for detecting inhibition of the release of ApoB-100-associated lipoproteins from liver cells was carried out in vitro using cultured liver cells, preferably using cells of the human line HepG2. These cells are grown under standard conditions in medium for the culture of eucaryotic cells, preferably in RPMI 1640 using 10% foetal calf serum. HepG2 cells synthesize and secrete into the culture supernatant ApoB-100-associated lipoprotein particles which in principle are synthesized in a similar manner to the VLDL and LDL particles which are to be found in the plasma.

These particles can be detected using an immunoassay for human LDL. This immunoassay is carried out using antibodies which have been induced in the rabbit against human LDL under standard conditions. The anti-LDL antibodies (rabbit anti-LDL-Ab) were purified by affinity chromatography on an immunosorbent using human LDL. These purified rabbit anti-LDL Ab are adsorbed on the surface of plastic. Expediently, this adsorption is carried out on the plastic surface of microtitre plates having 96 wells, preferably on MaxiSorp plates. If ApoB-100-associated particles are present in the supernatant of Hep-G2 cells, these can bind to the insolubilized rabbit anti-LDL Ab, and an immune complex is formed which is bound to the plastic surface. Unbound proteins are removed by washing. The immune complex located on the plastic surface is detected using monoclonal antibodies which have been induced against human LDL according to standard conditions and purified. These antibodies were conjugated with the enzyme peroxidase. Peroxidase converts the colourless substrate TMB into a coloured product in the presence of $H_2O_2$. After acidification of the reaction mixture using $H_2SO_4$, the specific light absorption at 450 nm is determined, which is a measure of the amount of ApoB-100-associated particles which have been secreted into the culture supernatant by the HepG2 cells.

Surprisingly, the compounds according to the invention inhibit the release of the ApoB-100-associated particles. The $IC_{50}$ value indicates at which substance concentration the light absorption is inhibited by 50% in comparison with the control (solvent control without substance).

TABLE 1

| Example No. | ApoB $IC_{50}$ [nM] |
| --- | --- |
| 112 | 4.0 |
| 113 | 58.0 |
| 114 | 39.0 |
| 115 | 240.0 |
| 117 | 3.0 |
| 118 | 7.0 |
| 119 | 11.0 |
| 120 | 28.0 |
| 121 | 36.0 |
| 122 | 48.0 |
| 123 | 8.0 |
| 126 | 41.0 |
| 129 | 34.0 |
| 130 | 25.0 |
| 131 | 135.0 |
| 132 | 743.0 |
| 133 | 5.0 |
| 136 | 23.0 |

TABLE 1-continued

| Example No. | ApoB $IC_{50}$ [nM] |
| --- | --- |
| 137 | 124.0 |
| 138 | 403.0 |
| 139 | 90.0 |
| 140 | 10.0 |
| 143 | 11.0 |
| 146 | 6.0 |
| 149 | 9.0 |
| 151 | 34.0 |
| 152 | 169.0 |
| 154 | 3.0 |
| 155 | 2.0 |
| 156 | 25.0 |
| 157 | 8.0 |
| 158 | 2.0 |
| 159 | 25.0 |
| 160 | 5.0 |
| 163 | 131.0 |
| 164 | 12.0 |
| 167 | 19.0 |
| 168 | 16.0 |
| 169 | 3.0 |
| 170 | 16.0 |
| 171 | 2.0 |
| 172 | 1.0 |
| 174 | 5.0 |
| 175 | 32.0 |
| 176 | 19.0 |
| 178 | 64.0 |
| 179 | 5.0 |
| 180 | 5.0 |
| 181 | 10.0 |
| 182 | 12.0 |
| 183 | 10.0 |
| 184 | 24.0 |
| 185 | 29.0 |
| 188 | 23.0 |
| 189 | 31.0 |
| 190 | 86.0 |
| 191 | 14.0 |
| 192 | 8.0 |
| 193 | 62.0 |
| 194 | 8.0 |
| 195 | 5.0 |
| 196 | 61.0 |
| 197 | 43.0 |
| 198 | 5.0 |
| 199 | 5.0 |
| 200 | 24.0 |
| 201 | 11.0 |
| 202 | 9.0 |
| 203 | 63.0 |
| 204 | 16.0 |
| 207 | 40.0 |
| 211 | 9.0 |
| 212 | 8.0 |
| 215 | 3.0 |
| 216 | 34.0 |
| 217 | 11.0 |
| 218 | 8.0 |
| 219 | 5.0 |
| 220 | 16.0 |
| 223 | 4.0 |
| 224 | 4.0 |
| 225 | 4.0 |
| 226 | 11.0 |
| 227 | 40.0 |

2. DETERMINATION OF VLDL SECRETION IN VIVO IN THE HAMSTER

The effects of the test substances on VLDL secretion in vivo is investigated in the hamster. To do this, golden hamsters are anaesthetized with Ketavet (83 mg/kg s.c.) and Nembutal (50 mg/kg i.p.) after premedication with atropine (83 mg/kg s.c.). When the animals have become reflex-free, the jugular vein is exposed and cannulated. 0.25 ml/kg of a 20% strength solution of Triton WR 1339 in physiological saline solution is then administered. This detergent inhibits the lipoprotein lipase and thus leads to an increase in the triglyceride level as a result of lack of catabolism of secreted VLDL particles. This triglyceride increase can be used as a measure of the VLDL secretion rate. Blood is taken from the animals before and one and two hours after administration of the detergent by puncture of the retroorbital venous plexus. The blood is incubated for two hours at room temperature, then overnight at 4° C. in order to finish clotting completely. It is then centrifuged at 10,000 g for 5 minutes. The triglyceride concentration in the serum thus obtained is determined with the aid of a modified commercially available enzyme test (Merckotest® triglyceride No. 14354). 100 µl of serum are mixed with 100 µl of test reagent in 96-hole plates and incubated at room temperature for 10 minutes. The optical density is then determined at a wavelength of 492 nM in an automatic plate-reading apparatus (SLT spectra). Serum samples having too high a triglyceride concentration are diluted with physiological saline solution. The triglyceride concentration contained in the samples is determined with the aid of a standard curve measured in parallel. Test substances are administered in this model either intravenously immediately before administration of the detergent or orally or subcutaneously before initiation of the anaesthesia.

TABLE 2

| Example No. | Triton hamster % TG inhibition 2 h after substance | Triton hamster % CH inhibition 2 h after substance |
|---|---|---|
| 129 | 25% at 6 mg/kg i.v. | 25% at 6 mg/kg i.v. |

3. INHIBITION OF INTESTINAL TRIGLYCERIDE ABSORPTION IN VIVO (RATS)

The substances which are to be investigated for their triglyceride absorption-inhibiting action in vivo are administered orally to male Wistar rats having a body weight of between 170 and 230 g. For this purpose, the animals are divided into groups of 6 animals 18 hours before administration of the substance and the feed is then withdrawn from them. Drinking water is available to the animals ad libitum. The animals of the control groups receive an aqueous tragacanth suspension or a tragacanth suspension which contains olive oil. The tragacanth-olive oil suspension is prepared using an Ultra-Turrax. The substances to be investigated are suspended directly before substance administration in a corresponding tragacanth-olive oil suspension, also using an Ultra-Turrax.

Before stomach tube application, blood is taken from each rat by puncture of the retroorbital venous plexus to determine the basal serum triglyceride content. The tragacanth suspension, the tragacanth-olive oil suspensions without substance (control animals) and the substances suspended in a corresponding tragacanth-olive oil suspension are then administered to the fasting animals using a stomach tube. Further taking of blood for the determination of the postprandial serum triglyceride rise is carried out, as a rule, 1,2 and 3 hours after stomach tube application.

The blood samples are centrifuged and, after recovering the serum, the triglycerides are determined photometrically using an EPOS analyzer 5060 (Eppendorf Geratebau, Netheler & Hinz GmbH, Hamburg). The triglycerides are determined by fully enzymatic means using a commercially available UV test.

The postprandial serum triglyceride increase is determined by subtraction of the triglyceride preliminary value of each animal from its corresponding postprandial triglyceride concentrations (1,2 and 3 hours after administration).

The differences (in mmol/l) at each time 1, 2 and 3 hours) are averaged in the groups, and the average values of the serum triglyceride increase (ΔTG) of the substance-treated animals are compared with the animals which only received the tragacanth-oil suspension.

Likewise, the serum triglyceride course of the control animals which received only tragacanth is calculated. The substance effect at each time (1, 2 or 3 hours) is determined as follows and given in Δ% of the oil-loaded control.

$$\Delta \% \text{ triglyceride increase} = \frac{\Delta TG_{substance} - \Delta TG_{tragacanth\ control}}{\Delta TG_{oil\ loading} - \Delta TG_{tragacanth\ control}} \times 100$$

Effect of 10 mg of test substance/kg of body weight p.o. on the triglyceride increase (Δ%) 2 h after a triglyceride loading in the serum of fasting rats. The serum triglyceride increase of fat-loaded control animals based on the serum triglyceride level of tragacanth control animals corresponds to 100%. n=6 animals per group.

TABLE 3

| Example No. | Absorption ED$_{50}$ or % inhibition (mg/kg p.o.) |
|---|---|
| 112 | 3 mg/kg |
| 114 | <2 mg/kg |
| 117 | 3 mg/kg |
| 123 | 2 mg/kg |
| 129 | 20 mg/kg |
| 130 | 5 mg/kg |
| 133 | 2 mg/kg |
| 136 | 2 mg/kg |
| 140 | >3 mg/kg |
| 143 | >3 mg/kg |
| 146 | >3 mg/kg |
| 149 | >3 mg/kg |
| 151 | 6 mg/kg |
| 154 | <2 mg/kg |
| 157 | >2 mg/kg |
| 160 | 3 mg/kg |
| 167 | >2 mg/kg |
| 169 | 2 mg/kg |
| 174 | <2 mg/kg |
| 178 | 3 mg/kg |
| 179 | >3 mg/kg |
| 182 | 2 mg/kg |
| 191 | >>3 mg/kg |
| 197 | 3 mg/kg |
| 201 | >3 mg/kg |
| 227 | >6 mg/kg |

Statistical assessment was carried out using student3 s t test after prior checking of the variances for homogeneity.

Substances which at one point statistically significantly (p<0.05) reduce the postprandial serum triglyceride increase by at least 30%, compared with the untreated control group, are regarded as pharmacologically active.

4. INHIBITION OF VLDL SECRETION IN VIVO (RAT)

The action of the test substances on VLDL secretion is also investigated in the rat. To do this, 500 mg/kg of body weight (2.5 ml/kg) of Triton WR-1339, dissolved in physiological saline solution, are administered to rats intravenously in the tail vein. Triton WR-1339 inhibits lipoprotein lipase and thus leads through inhibition of VLDL catabolism to an increase in the triglyceride and cholesterol level. These increases can be used as a measure of the VLDL secretion rate.

Blood is taken from the animals before and one and two hours after administration of the detergent by puncture of the retroorbital venous plexus. The blood is incubated at room temperature for 1 h for clotting and the serum is recovered by centrifugation at 10,000 g for 20 s. The triglycerides are then determined photometrically at a wavelength of 540 nm by means of a commercially available coupled enzyme test (Sigma Diagnostics®, No. 339). Measurement is carried out with the aid of a likewise coupled enzyme test (Boehringer Mannheim®, No. 1442350) at a wavelength of 546 nm. Samples with triglyceride or cholesterol concentrations which exceed the measuring range of the methods are diluted with physiological saline solution. The respective serum concentrations are determined with the aid of standard series measured in parallel. Test substances are administered orally, intravenously or subcutaneously immediately after the Triton injection.

TABLE 4

| Ex. No. | Triton rat % TG inhibition (p.o.) 2 h after substance |
|---|---|
| 112 | 17.0% at 3 mg/kg (n.s.) |
| 114 | 14.1% at 3 mg/kg (n.s.) |
| 117 | 25% at 3 mg/kg (n.s.) |
| 130 | 36% at 20 mg/kg |
| 136 | 28% at 3 mg/kg |
| 154 | (−4%) at 3 mg/kg (n.s.) |
| 157 | 11.3% at 3 mg/kg |
| 169 | 59.4% at 10 mg/kg |
| 169 | 41% at 5 mg/kg |
| 169 | 28% at 3 mg/kg |
| 175 | 9.8% at 3 mg/kg (n.s.) |
| 176 | 6.2% at 3 mg/kg (n.s.) |
| 227 | (−8%) at 3 mg/kg (n.s.) |

The invention additionally relates to the combination of substituted xanthines of the general formula (I) with a glucosidase and/or amylase inhibitor for the treatment of familial hyperlipidaemias, obesity (adiposity) and diabetes mellitus. Glucosidase and/or amylase inhibitors in the context of the invention are, for example, acarbose, adiposine, voglibose, miglitol, emiglitate, MDL-25637, camiglibose, MDL-73945, tendamistat, AI-3688, trestatin, pradimilin-Q and salbostatin.

The combination of acarbose, miglitol, emiglitate or voglibose with one of the abovementioned compounds of the general formula (I) according to the invention is preferred.

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this context, the therapeutically active compound should in each case be present in a concentration of approximately 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, if water is used as a diluent organic solvents can optionally be used as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proved advantageous in the case of intravenous administration to administer amounts of approximately 0.001 to 1 mg/kg, preferably approximately 0.01 to 0.5 mg/kg of body weight to achieve effective results, and in the case of oral administration the dosage is approximately 0.01 to 20 mg/kg, preferably 0.1 to 10 mg/kg of body weight.

In spite of this, it may, if appropriate, be necessary to depart from the amounts mentioned, namely depending on the body weight or on the type of administration route, on the individual behaviour towards the medicament, the manner of its formulation and the time or interval at which administration takes place. Thus, in some cases it may be adequate to manage with less than the abovementioned minimum amounts, while in other cases the upper limit mentioned has to be exceeded. In the case of the administration of relatively large amounts, it may be advisable to divide these into several individual doses over the course of the day.

ABBREVIATIONS USED

| | | |
|---|---|---|
| Ac | = | acetyl |
| bs | = | broad singlet |
| Bn | = | benzyl |
| Bz | = | benzoyl |
| CI | = | chemical ionization |
| cDec | = | cyclodecyl |
| cDodec | = | cyclododecyl |
| cHept | = | cycloheptyl |
| cHex | = | cyclohexyl |
| cNon | = | cyclononyl |
| cOct | = | cyclooctyl |
| cPent | = | cyclopentyl |
| cPr | = | cyclopropyl |
| cUndec | = | cycloundecyl |
| d | = | doublet |
| DCC | = | dicyclohexylcarbodiimide |
| DCCI | = | N'-(3-dimethylaminopropyl)-N'-ethylcarbodiimide |
| dd | = | doublet doublets |
| DDQ | = | 2,3-dichloro-5,6-dicyano-1,4-benzoquinone |
| dia | = | diastereomer |
| DMAP | = | 4-(N,N-dimethylamino)pyridine |
| DMF | = | N,N-dimethylformamide |
| DMSO | = | dimethyl sulphoxide |
| EI | = | electron impact ionization |
| ent | = | enantiomer |
| Et | = | ethyl |
| FAB | = | fast atom bombardment |
| HOBT | = | 1-hydroxy-1H-benzotriazole |
| Hz | = | Hertz |
| iBu | = | isobutyl |
| iPr | = | isopropyl |
| m | = | multiplet |
| Me | = | methyl |
| Mes | = | mesyl |
| NBS | = | bromosuccinimide |
| nBu | = | normal benzyl |
| nPr | = | normal propyl |
| Ph | = | phenyl |
| PPA | = | polyphosphoric acid |
| pTol | = | para-tolyl |
| pTos | = | para-tosyl |
| rac | = | racemate |
| RT | = | room temperature |
| s | = | singlet |
| sBu | = | secondary butyl |

-continued

| tBu | = | tertiary butyl |
| --- | --- | --- |
| t | = | triplet |
| TFA | = | trifluoroacetic acid |
| THF | = | tetrahydrofuran |
| TMS | = | tetramethylsilane |

SOLVENT MIXTURES USED

| Petroleum ether:acetone | = | 1:1 | (A) |
| --- | --- | --- | --- |
| Petroleum ether:ethyl acetate | = | 20:1 | (B) |
| Petroleum ether:ethyl acetate | = | 10:1 | (C) |
| Petroleum ether:ethyl acetate | = | 5:1 | (D) |
| Petroleum ether:ethyl acetate | = | 3:1 | (E) |
| Petroleum ether:ethyl acetate | = | 2:1 | (F) |
| Petroleum ether:ethyl acetate | = | 1:1 | (G) |
| Petroleum ether:ethyl acetate | = | 1:2 | (H) |
| Dichloromethane (100%) | = | | (I) |
| Dichloromethane:methanol | = | 50:1 | (J) |
| Dichloromethane:methanol | = | 20:1 | (K) |
| Dichloromethane:methanol | = | 10:1 | (L) |
| Dichloromethane:ethyl acetate | = | 1:1 | (M) |
| Dichloromethane:ethanol | = | 50:1 | (N) |
| Ethyl acetate:methanol | = | 10:1 | (O) |
| Toluene (100%) | = | | (P) |
| Toluene:ethyl acetate | = | 1:1 | (Q) |
| Toluene:ethyl acetate | = | 8:1 | (R) |
| Toluene:ethyl acetate | = | 9:1 | (S) |
| Petroleum ether:ethyl acetate | = | 4:1 | (T) |

ADDITIONS

The following marks are valid for all tables which follow:
*=EI #=CI

EXAMPLE I (Method A)

1,3-Dimethyl-8-(4-methyl)phenyl-xanthine

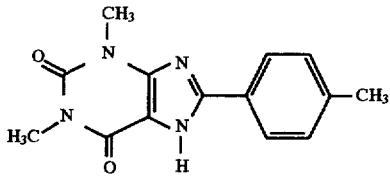

8.5 g (50 mmol) of 5,6-diamino-1,3-dimethyluracil hydrate were dissolved in ethanol (180 ml) under reflux. A solution of 6.0 g (50 mmol) of p-tolylaldehyde and 4.5 g of acetic acid in ethanol (50 ml) was added to this solution. The mixture was heated under reflux for 1 hour, cooled to room temperature and filtered with suction. The crystals were washed with diethyl ether.

The crystals thus obtained were initially introduced and treated with 36.6 g (210 mmol) of diethyl azodicarboxylate. The mixture was warmed at 90° C. for 5 min, a solid being precipitated. The solution was cooled to room temperature and diluted with ethanol (100 ml). The solid which was precipitated was filtered off with suction, washed with diethyl ether and dried in vacuo.

Yield 10.9 g (81%);
$R_f$=0.56 (dichloromethane:methanol, 20:1);
M.p.=>240° C.;
Mass (calculated) for $C_{14}H_{14}N_4O_2$=270.30, mass spectrum (EI, rel. intensity) 270 (100%);
$^1$H NMR (200 MHz, pyridine-$D_5$) δ8.29 (d, J=8.62 Hz, 2 H), 7.33 (d, J=7.89 Hz, 2 H), 4.98 (bs, 1 H), 3.72 (s, 3 H), 3.53 (s, 3 H), 2.29 (s, 3 H).

EXAMPLE II (Method B)

1,3-Dimethyl-8-[1-(3-chlorophenyl)methyl]xanthine

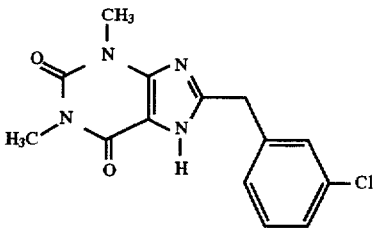

11.94 g (70 mmol) of 3-chlorophenylacetic acid were dissolved in 100 ml of dichloromethane, treated with a drop of DMF and cooled to 0° C. 8.74 g (73.5 mmol) of thionyl chloride were slowly added to this solution and it was stirred until the evolution of gas was complete (about 1 h), the reaction mixture being allowed to warm to room temperature.

11.91 g (70 mmol) of 5,6-diamino-1,3-dimethyluracil hydrate were initially introduced into 1M NaOH (150 ml) and water (350 ml) and warmed to 45° C. until a homogeneous solution resulted. This solution was cooled to room temperature and the acid chloride solution (see above) was added with vigorous stirring. The mixture was stirred at room temperature for a further 16 h. The solid which was precipitated was filtered off with suction and washed with water.

This solid was suspended in methanol (400 ml) and heated under reflux for 1 h with 4M NaOH (400 ml). After cooling to room temperature, the solution was acidified to pH 3 using conc. HCl, the desired product being precipitated. The solid which was precipitated was filtered off with suction, washed with water and methanol and dried in a recirculating air cabinet.

Yield 17.1 g (80%);
$R_f$=0.57 (dichloromethane:methanol, 10:1);
M.p.=>240° C;
Mass (calculated) for $C_{14}H_{13}ClN_4O_2$=304.74, mass spectrum (EI, rel. intensity) 304 (100%);
$^1$H NMR (200 MHz, trifluoroacetic acid-$D_1$) δ7.36–7.30 (m, 3 H), 7.20 (m, 1 H), 4.50 (s, 2 H), 3.74 (s, 3 H), 3.52 (s, 3 H).

EXAMPLE III (Method C)

1,3-Diethylxanthine

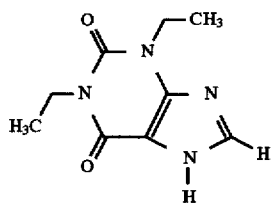

5.0 g (25 mmol) of 5,6-diamino-1,3-diethyluracil and 475 mg (2.5 mmol) of p-toluenesulphonic acid were dissolved in trimethyl orthoformate (50 ml). The mixture was heated at reflux for 1 hour, then cooled and filtered with suction. As a polar impurity was present, the substance was purified by chromatography on silica gel:

Yield 3.5 g (67%);
R$_f$=0.15 (dichloromethane:methanol, 20:1);
M.p.=218°–220° C.;
Mass (calculated) for C$_9$H$_{12}$N$_4$O$_2$=208.23, mass spectrum (EI, rel intensity) 208 (100%);

$^1$H NMR (200 MHz, DMSO-D$_6$)δ13.55 (bs, 1 H), 8.05 (s, 1 H), 4.04 (q, J=7.07 Hz, 2 H), 3.93 (q, J=7.02 Hz, 2 H), 1.23 (t, J=7.03 Hz, 3 H), 1.13 (t, J=7.01 Hz, 3 H).

The compounds shown in Table I were prepared by the methods shown there:

TABLE 1

| Example No. | R$^4$ | R$^3$ | R$^5$ | T | V | R$_f$* | M.p. (°C.) | Method | Mass spectrum | Yield (% of theory) |
|---|---|---|---|---|---|---|---|---|---|---|
| IV | CH$_3$ | CH$_3$ | CH$_3$ | O | O | 0.57(L) | >240 | C | *194(100%) | 50 |
| V | CH$_3$ | CH$_3$ | C$_2$H$_5$ | O | O | 0.56(K) | >240 | C | *208(100%) | 46 |
| VI | CH$_3$ | CH$_3$ | cPro | O | O | 0.35(K) | >240 | A | *220(100%) | 47 |
| VII | CH$_3$ | CH$_3$ | —CH$_2$cHex | O | O | 0.61(L) | 238 | B | *276(40%) 194(100%) | 72 |
| VIII | CH$_3$ | CH$_3$ | (2-thienylmethyl) | O | O | 0.80(L) | >240 | B | 276(100%) | 47 |
| IX | CH$_3$ | CH$_3$ | (o-tolyl) | O | O | 0.67(K) | >240 | A | *270(100%) | 82 |
| X | CH$_3$ | CH$_3$ | (m-tolyl) | O | O | 0.86(L) | >240 | A | *270(100%) | 79 |
| XI | CH$_3$ | CH$_3$ | (2,4-dimethylphenyl) | O | O | 0.80(L) | >240 | A | *284(100%) | 69 |
| XII | CH$_3$ | CH$_3$ | (4-phenylphenyl) | O | O | 0.85(L) | >240 | B | *332(100%) | 73 |
| XIII | CH$_3$ | CH$_3$ | (4-chlorophenyl) | O | O | 0.77(L) | >240 | A | *290(100%) | 73 |
| XIV | CH$_3$ | CH$_3$ | (4-CF$_3$-phenyl) | O | O | 0.75(L) | >240 | A | *324(100%) | 69 |
| XV | CH$_3$ | CH$_3$ | (4-OCH$_3$-phenyl) | O | O | 0.80(L) | >240 | A | *286(100%) | 76 |
| XVI | CH$_3$ | CH$_3$ | (4-N(CH$_3$)$_2$-phenyl) | O | O | — | >240 | A | *299(100%) | 77 |

TABLE 1-continued

[Structure: imidazo-pyrimidine core with R³ on N, T substituent, R⁴ on N, V substituent, and R⁵ on imidazole]

| Example No. | R⁴ | R³ | R⁵ | T | V | $R_f$* | M.p. (°C.) | Method | Mass spectrum | Yield (% of theory) |
|---|---|---|---|---|---|---|---|---|---|---|
| XVII | CH₃ | CH₃ | –C₆H₄–N(C₂H₅)₂ | O | O | | >250 | A | #328(100%) | 81 |
| XVIII | CH₃ | CH₃ | 2-pyridyl | O | O | 0.33(K) | >240 | A | 257(100%) | 58 |
| XIX | CH₃ | CH₃ | 3-pyridyl | O | O | 0.26(K) | >240 | A | *257(100%) | 66 |
| XX | CH₃ | CH₃ | 4-pyridyl | O | O | 0.15(K) | >240 | A | *258(100%) | 21 |
| XXI | CH₃ | CH₃ | 3-thienyl | O | O | 0.40(K) | >240 | A | *262(100%) | 80 |
| XXII | CH₃ | CH₃ | 2-thienyl | O | O | | >240 | A | | 88 |
| XXIII | CH₃ | CH₃ | 3-methyl-2-thienyl | O | O | 0.30(K) | >240 | A | 276(100%) | 78 |
| XXIV | CH₃ | CH₃ | 5-methyl-2-thienyl | O | O | 0.38(K) | >240 | A | 276(100%) | 75 |
| XXV | CH₃ | CH₃ | 3-bromo-5-methyl-2-thienyl | O | O | 0.54(K) | >240 | A | 341(100%) | 83 |
| XXVI | CH₃ | CH₃ | –CH=CH–C₆H₅ | O | O | 0.69(K) | >240 | A | 283(100%) | 70 |
| XXVII | CH₃ | CH₃ | 2-methylbenzyl | O | O | 0.68(L) | >240 | B | *284(100%) | 68 |
| XXVIII | CH₃ | CH₃ | 3-methylbenzyl | O | O | 0.68(L) | >240 | B | *284(100%) | 64 |

TABLE 1-continued

| Example No. | R⁴ | R³ | R⁵ | T | V | R_f* | M.p. (°C.) | Method | Mass spectrum | Yield (% of theory) |
|---|---|---|---|---|---|---|---|---|---|---|
| XXIX | CH₃ | CH₃ | 4-methylbenzyl (-CH₂-C₆H₄-CH₃) | O | O | 0.28(K) | >240 | B | *284(100%) | 64 |
| XXX | CH₃ | CH₃ | 4-phenylbenzyl (-CH₂-C₆H₄-Ph) | O | O | 0.78(L) | >240 | B | *346(100%) | 47 |
| XXXI | CH₃ | CH₃ | 2-chlorobenzyl (-CH₂-C₆H₄-Cl) | O | O | 0.57(L) | >240 | B | *304(100%) | 71 |
| XXXII | CH₃ | CH₃ | 4-fluorobenzyl (-CH₂-C₆H₄-F) | O | O | 0.64(L) | >240 | B | *288(100%) | 49 |
| XXXIII | CH₃ | CH₃ | 2-methoxybenzyl (-CH₂-C₆H₄-OCH₃) | O | O | 0.61(L) | >240 | B | *300(100%) | 64 |
| XXXIV | CH₃ | CH₃ | 3-methoxybenzyl (-CH₂-C₆H₄-OCH₃) | O | O | 0.64(K) | >240 | B | *300(100%) | 66 |
| XXXV | CH₃ | CH₃ | 4-methoxybenzyl (-CH₂-C₆H₄-OCH₃) | O | O | 0.27(K) | >240 | B | *300(100%) | 23 |
| XXXVI | CH₃ | CH₃ | -CH(Ph)(C₆H₅) | O | O | 0.74(K) | 143–45 | A | *346(100%) | 7 |
| XXXVII | C₂H₅ | C₂H₅ | CH₃ | O | O | 0.83(K) | 231–33 | C | *222(100%) | 54 |
| XXXVIII | C₂H₅ | C₂H₅ | C₂H₅ | O | O | 0.71(K) | 193–94 | C | *236(100%) | 67 |
| XXXIX | C₂H₅ | C₂H₅ | cPro | O | O | 0.69(L) | 217–18 | A | #249(100%) | 39 |
| XL | C₂H₅ | C₂H₅ | 4-methylphenyl (-C₆H₄-CH₃) | O | O | 0.76(L) | >240 | A | #299(100%) | 70 |
| XLI | C₂H₅ | C₂H₅ | 2-thienyl | O | O | 0.67(L) | >240 | A | #291(100%) | 82 |
| XLII | CH₃ | CH₃ | CH₃ | S | O | 0.30(K) | >240 | C | *210(100%) | 51 |
| XLIII | CH₃ | CH₃ | C₂H₅ | S | O | 0.62(K) | >240 | C | *224(100%) | 78 |

TABLE 1-continued

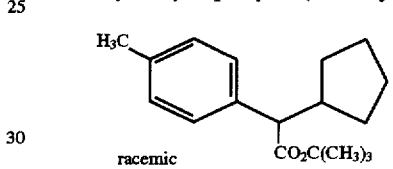

| Example No. | R⁴ | R³ | R⁵ | T | V | $R_f$* | M.p. (°C.) | Method | Mass spectrum | Yield (% of theory) |
|---|---|---|---|---|---|---|---|---|---|---|
| XLIV | $CH_3$ | $CH_3$ | (2-thienyl) | S | O | 0.79(K) | >240 | A | *278(100%) | 51 |
| XLV | $CH_3$ | $CH_3$ | (4-methylphenyl) | S | O | 0.80(K) | >240 | A | *286(100%) | 59 |

EXAMPLE XLVI

Methyl 2-(R&S)-phenyl-2-(4-methyl)phenylacetate

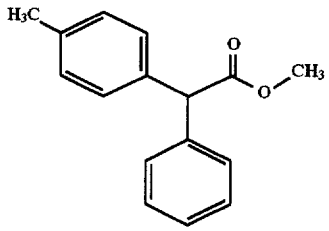

21.0 g (100 mmol, Apin) of 2-phenyl-1-(4-methyl)phenyl-1-oxoethane and 38.8 g (120 mmol) of iodobenzene diacetate were dissolved in 300 ml of trimethyl orthoformate. 19.6 g of conc. sulphuric acid were added to this solution, and the solution was warmed at 60° C. for 6 hours. The solution was cooled to room temperature, diluted with water (100 ml) and extracted with diethyl ether. The combined organic phases were dried over sodium sulphate and concentrated in a rotary evaporator. The residue was purified by column chromatography.

Yield 13.1 g (55%);

$R_f$=0.33 (petroleum ether:ethyl acetate, 20:1);

Mass (calculated for $C_{16}H_{16}O_2$=240.30, mass spectrum (FAB, rel. intensity) 241 (25%), 181 (100%);

¹H NMR (200 MHz, $CDCl_3$)δ7.3–7.10 (m, 9 H), 4.99 (s, 1 H), 3.73 (s, 3 H), 2.31 (s, 3 H).

EXAMPLE XLVII tert-Butyl 2-cyclopentyl-2-(4-methylphenyl)acetate (racemic structure shown)

33.5 g (0.3 mol) of potassium tert-butoxide are initially introduced into 100 ml of anhydrous DMF at 0° C., and 51.6 g (0.25 mol) of tert-butyl 4-methylphenyl-acetate in 250 ml of anhydrous DMF are added dropwise. The mixture is stirred at 0° C. for 30 min and 32.2 ml (0.3 mol) of cyclopentyl bromide in 150 ml of anhydrous DMF are added dropwise at 5°–15° C. and it is stirred at 25° C. for 20 h. After concentrating, the residue is partitioned between water and diethyl ether, and the ether phase is dried over sodium sulphate and concentrated. The product crystallizes out.

Yield: 67 g (97.5% of theory)

Melting point: 51°–53° C.

The compounds of Table II are prepared analogously to the procedure of Example XLVII:

TABLE II

| Ex. No. | R¹ | R¹⁸ | $R_f$* |
|---|---|---|---|
| XLIII | (R&S) iPr | $CH_3$ | 0.86 (S) |
| IL | (R&S) iBu | tBu | 0.84 (R) |
| L | (R&S) cPent | $CH_3$ | 0.59 (C) |
| LI | (R&S) cHex | $CH_3$ | 0.38 (B) |
| LII | (R&S) cHex | tBu | 0.71 (P) |
| LIII | (R&S) cHept | $CH_3$ | 0.57 (P) |
| LIV | (R&S) cHept | tBu | 0.32 (P) |

EXAMPLE LV tert-butyl 2-(4-bromomethyl-phenyl)-2-cyclopentyl-acetate

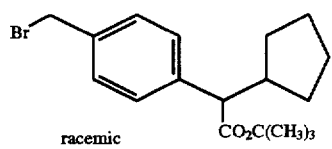

racemic 27.4 g (0.1 mol) of the compound from Example XLVII are dissolved in 200 ml of tetrachloromethane and heated to boiling. After addition of 0.82 g of azobisisobutyronitrile, 18.7 g (0.105 mol) of N-bromosuccinimide are added in portions and the mixture is then refluxed for 1 h, cooled to 0° C. and succinimide is filtered off. After concentrating the filtrate, the product precipitates out. It is washed with petroleum ether (40:60) and dried.
Yield: 20 g (57% of theory);
M.p.: 73°–76° C.

The compounds of Table III are prepared analogously to the procedure of Example LV:

TABLE III

| Ex. No. | $R^1$ | $R^{19}$ | $R_f^*$ | Starting compound |
|---|---|---|---|---|
| LVI | (R&S) iPr | $CH_3$ | 0.78 (I) | XLIII |
| LVII | (R&S) iBu | tBu | 0.86 (I) | IL |
| LVIII | (R&S) cPent | $CH_3$ | 0.63 (C) | L |
| LIX | (R&S) cHex | $CH_3$ | 0.74 (I) | LI |
| LX | (R&S) cHex | tBu | 0.58 (C) | LII |
| LXI | (R&S) cHept | $CH_3$ | 0.59 (P) | LIII |
| LXII | (R&S) cHept | tBu | 0.84 (I) | LIV |
| LXIII | (R&S) Ph | $CH_3$ | 0.74 (I) | XLVI |

PREPARATION EXAMPLES

Example 1 tert-Butyl 2-(R&S)-cyclopentyl-2-[4-(1,3-dimethyl-2,6-dioxo-8-(4-methyl)phenyl-1,2,3,6-tetrahydro-purin-7-ylmethyl)phenyl]acetate

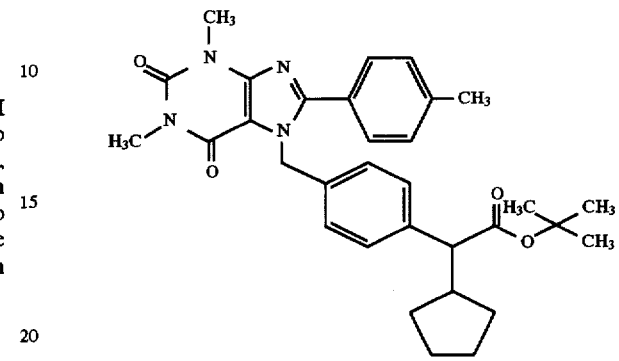

5.4 g (25 mmol) of the compound from Example I were suspended in DMF (100 ml) at 22° C. and treated with 0.8 g (60% in paraffin, 22 mmol) of NaH. After 30 min at 40° C., the solution was treated with the compound from Example LV. The mixture was stirred at room temperature for a further 16 h. Water was added and the precipitate obtained was filtered off with suction. The moderately moist solid was stirred with dichloromethane and filtered off with suction.
Yield 9.3 g (88%);
$R_f$=0.48 (dichloromethane:methanol, 20:1);
Mass (calculated) for $C_{32}H_{38}N_4O_4$=542.68, mass spectrum (CI ($NH_3$), rel. intensity) 560 (25%, M+$NH_4$), 543 (100%);
$^1$H NMR (300 MHz, $CDCl_3$) δ7.42 (d, 2 H), 7.28–7.20 (m, 4 H), 6.95 (d, 2 H), 5.60 (s, 2 H), 3.61 (s, 3 H), 3.40 (s, 3 H), 3.10 (d, 1 H), 2.42 (m, 1 H), 2.40 (s, 3 H), 1.90 (m, 1 H), 1.70–1.20 (m, 6 H), 1.41 (s, 9 H), 0.95 (m, 1 H).

The compounds shown in Tables 1, 2 and 3 are prepared in analogy to the procedure of Example 1:

TABLE 1

| Ex. No. | $R^1$ | $R^5$ | $R^{20}$ | $R_f^*$ | M.p. (°C.) | Mass spectrum | Yield (% of theory) | Starting compound |
|---|---|---|---|---|---|---|---|---|
| 2 | (R&S)cPent | H | tBu | 0.54 (K) | 134 | 453(100%) | 65 | |
| 3 | (R&S)cPent | Br | tBu | 0.40 (J) | 162 | 531(25%) 57(100%) | 74 | |
| 4 | (R&S)cPent | $CH_3$ | tBu | 0.23 (J) | 162 | 467(100%) | 68 | IV |
| 5 | (R&S)cPent | Et | tBu | 0.22 (J) | 145 | 481(40%) 57(100%) | 50 | V |
| 6 | (R&S)cPent | cPr | tBu | 0.23 (J) | 74 | 493(100%) | 70 | VI |
| 7 | (R&S)cPent | cPent | tBu | 0.30 (J) | 63 (Foam) | 521(20%) 57(100%) | 68 | |
| 8 | (R&S)cPent | —$CH_2$cHex | tBu | 0.38 (J) | 112 | 549(80%) | 71 | VII |

TABLE 1-continued
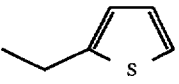
| Ex. No. | R¹ | R⁵ | R²⁰ | $R_f$* | M.p. (°C.) | Mass spectrum | Yield (% of theory) | Starting compound |
|---|---|---|---|---|---|---|---|---|
| | | | | | | 57(100%) | | |
| 9 | (R&S)cPent | 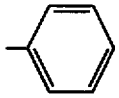 | CH₃ | 0.41 (J) | 148 | 508(100%) | 66 | |
| 10 | (R&S)cPent | 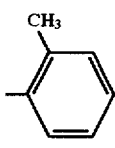 | tBu | 0.11 (T) | | | 84 | VIII |
| 11 | (R&S)cPent | 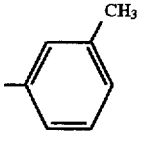 | tBu | 0.31 (J) | 105 | 543(60%) 57(100%) | 60 | IX |
| 12 | (R&S)cPent | 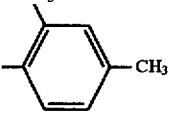 | tBu | 0.37 (J) | 98 | 543(100%) | 64 | X |
| 13 | (R&S)cPent | 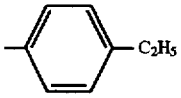 | tBu | 0.39 (J) | 88 (Foam) | 557(100%) | 66 | XI |
| 14 | (R&S)cPent | 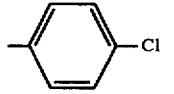 | CH₃ | 0.46 (J) | 104 (Foam) | 563(100%) | 52 | XII |
| 15 | (R&S)cPent | 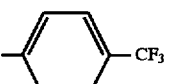 | tBu | 0.24 (J) | 90 (Foam) | 563(80%) 57(100%) | 40 | XIII |
| 16 | (R&S)cPent | 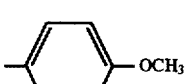 | tBu | 0.26 (J) | — | 597(80%) 57(100%) | 53 | XIV |
| 17 | (R&S)cPent | 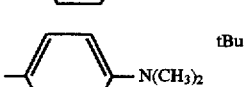 | tBu | 0.36 (J) | 96 (Foam) | *559(100%) | 51 | XV |
| 18 | (R&S)cPent |  | tBu | 0.06 (J) | (Foam) | 571(80%) 298(100%) | 36 | XVI |

TABLE 1-continued

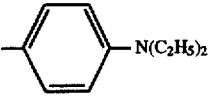

| Ex. No. | R¹ | R⁵ | R²⁰ | R_f* | M.p. (°C.) | Mass spectrum | Yield (% of theory) | Starting compound |
|---|---|---|---|---|---|---|---|---|
| 19 | (R&S)cPent |  4-N(C₂H₅)₂-phenyl | tBu | 0.3 (J) | 84 (Foam) | 600(100%) 599(100%) | 61 | XVII |
| 20 | (R&S)cPent |  2-pyridyl | tBu | 0.41 (J) | 155 | 529(40%) 473(100%) | 57 | XVIII |
| 21 | (R&S)cPent |  3-pyridyl | tBu | 0.25 (J) | — | 530(50%) 57(100%) | 20 | XIX |
| 22 | (R&S)cPent |  4-pyridyl | tBu | 0.15 (K) | >240 | 530(100%) | 52 | XX |
| 23 | (R&S)cPent |  3-thienyl | tBu | 0.41 (J) | 173 | 535(40%) 57(100%) | 68 | XXI |
| 24 | (R&S)cPent | 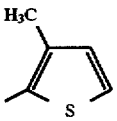 2-thienyl | tBu | 0.26 (E) | — | 535(100%) 534(80%) | 60 | XXII |
| 25 | (R&S)cPent | 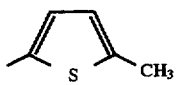 3-CH₃-2-thienyl | tBu | 0.52 (J) | 193 | 549(70%) 57(100%) | 66 | XXIII |
| 26 | (R&S)cPent |  5-CH₃-2-thienyl | tBu | 0.45 (J) | 78 (Foam) | 549(50%) 57(100%) | 53 | XXIV |
| 27 | (R&S)cPent | 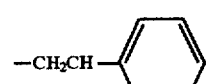 3-Br-5-thienyl | tBu | 0.44 (J) | 165 | 615(60%) 57(100%) | 54 | XXV |
| 28 | (R&S)cPent | —CH₂CH-phenyl | tBu | 0.79 (G) | 207 | 555(75%) 57(100%) | 59 | XXVI |

TABLE 2

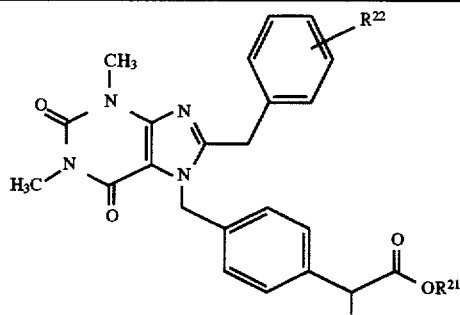

| Ex. No. | $R^1$ | $R^{21}$ | $R^{22}$ | $R_f$* | M.p. (°C.) | Mass spectrum | Yield (% of theory) | Starting compound |
|---|---|---|---|---|---|---|---|---|
| 29 | (R&S)cPent | tBu | H | 0.26 (J) | 136 | 543(60%) 57(100%) | 68 | |
| 30 | (R&S)cHex | CH₃ | H | 0.21 (J) | 131 | 515(100%) | 80 | |
| 31 | (R&S)cHept | tBu | H | 0.76 (K) | 82 | 571(100%) | 86 | |
| 32 | (R&S) Phenyl | CH₃ | H | 0.23 (J) | 92 | 509(100%) | 44 | |
| 33 | (R&S)cPent | tBu | 2-CH₃ | 0.29 (J) | 148 | 557(100%) | 55 | XXVII |
| 34 | (R&S)cPent | tBu | 3-CH₃ | 0.40 (J) | 65 (Foam) | 557(60%) 57(100%) | 51 | XXVIII |
| 35 | (R&S)cPent | tBu | 4-CH₃ | 0.17 (J) | 165 | 557(100%) | 56 | XXIX |
| 36 | (R&S)cPent | tBu | 4-Phenyl | 0.35 (J) | 90 (Foam) | 619(60%) 57(100%) | 58 | XXX |
| 37 | (R&S)cPent | tBu | 2-Cl | 0.26 (J) | 156 | 577(40%) 57(100%) | 61 | XXXI |
| 38 | (R&S)cPent | tBu | 3-Cl | 0.21 (J) | 135 | 577(100%) | 40 | II |
| 39 | (R&S)cPent | tBu | 4-F | 0.17 (J) | 162 | 561(100%) 505(100%) | 60 | XXXII |
| 40 | (R&S)cPent | tBu | 2-OCH₃ | 0.21 (J) | 138 | 573(40%) 57(100%) | 64 | XXXIII |
| 41 | (R&S)cPent | tBu | 3-OCH₃ | 0.19 (J) | — | 573(60%) 57(100%) | 72 | XXXIV |
| 42 | (R&S)cPent | tBu | 4-OCH₃ | 0.28 (J) | 75 (Foam) | 573(80%) 57(100%) | 48 | XXXV |

TABLE 3

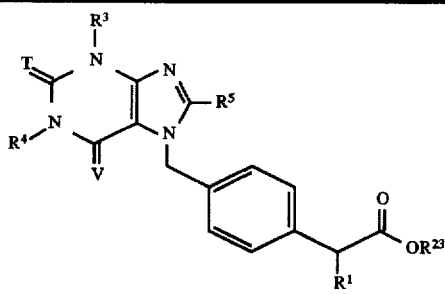

| Ex. No. | $R^1$ | $R^3$ | $R^4$ | $R^5$ | $R^{23}$ | T | V | $R_f$* | M.p. (°C.) | Mass spectrum | Yield (% of theory) | Starting compound |
|---|---|---|---|---|---|---|---|---|---|---|---|---|
| 43 | (R&S) cPent | C₂H₅ | C₂H₅ | H | tBu | O | O | 0.28 (J) | 01 | 481(100%) 57(90%) | 76 | III |
| 44 | (R&S) cPent | C₂H₅ | C₂H₅ | CH₃ | tBu | O | O | 0.22 (J) | 167 | 495(50%) 57(100%) | 66 | XXXVII |
| 45 | (R&S) cPent | C₂H₅ | C₂H₅ | C₂H₅ | tBu | O | O | 0.34 (J) | 121–24 | 509(100%) 57(80%) | 69 | XXXVIII |
| 46 | (R&S) cPent | C₂H₅ | C₂H₅ | cPro | CH₃ | O | O | 0.40 (J) | 128 | 479(80%) 55(100%) | 49 | XXIX |
| 47 | (R&S) cPent | C₂H₅ | C₂H₅ | Phenyl | CH₃ | O | O | 0.26 (J) | 58 (Foam) | 515(100%) | 57 | |
| 48 | (R&S) cPent | C₂H₅ | C₂H₅ | 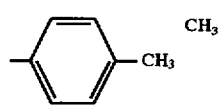 | CH₃ | O | O | 0.40 (J) | 58 (Foam) | 529(100%) | 46 | XL |

TABLE 3-continued

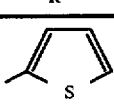

| Ex. No. | R¹ | R³ | R⁴ | R⁵ | R²³ | T | V | $R_f$* | M.p. (°C.) | Mass spectrum | Yield (% of theory) | Starting compound |
|---|---|---|---|---|---|---|---|---|---|---|---|---|
| 49 | (R&S) cPent | C₂H₅ | C₂H₅ | 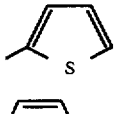 | CH₃ | O | O | 0.58 (J) | 166 | 521(85%) 55(100%) | 65 | XLI |
| 50 | (R&S) cPent | CH₃ | tBu | H | tBu | O | O | 0.64 (J) | — | 495(60%) 57(100%) | 69 | |
| 51 | (R&S) cPent | CH₃ | CH₃ | CH₃ | tBu | S | O | 0.43 (J) | 158–60 | 483(60%) 427(100%) 57(100%) | 68 | XLII |
| 52 | (R&S) cPent | CH₃ | CH₃ | C₂H₅ | tBu | S | O | 0.60 (J) | 178–82 | 497(80%) 441(100%) 57(100%) | 68 | XLIII |
| 53 | (R&S) cPent | CH₃ | CH₃ | 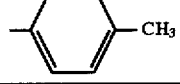 | tBu | S | O | 0.84 (J) | 180–83 | 551(20%) 57(100%) | 57 | XLIV |
| 54 | (R&S) cPent | CH₃ | CH₃ | ⟨phenyl-CH₃⟩ | tBu | S | O | 0.88 | 158–62 | 559(20%) 57(100%) | 68 | XLV |

Example 55

2-(R&S)-Cyclopentyl-2-[4-(1,3-dimethyl-2,6-dioxo-8-(3-hydroxy-phenyl)-methyl-1,2,3,6-tetrahydro-purin-7-ylmethyl)phenyl]acetate

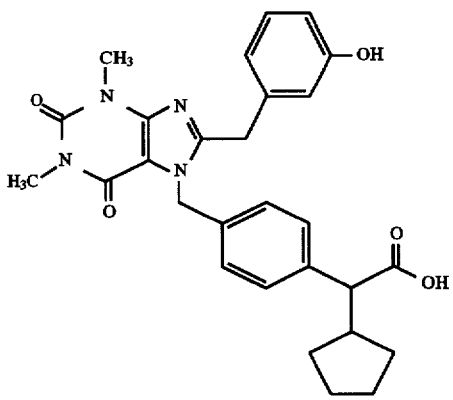

5.26 g (9.18 mmol) of the compound from Example 41 are dissolved in 50 ml of CH₂Cl₂ and the solution is cooled to −78° C. 45.9 ml (45.9 mmol; 1 molar in CH₂Cl₂) of boron tribromide are slowly added to this. The mixture is subsequently stirred at room temperature for 2 hours. It is then cooled again to 0° C. with an ice bath and treated with 50 ml of methanol. It is subsequently stirred overnight at room temperature. The solvent is evaporated using a rotary evaporator, and the residue is taken up in CH₂Cl₂ and water and extracted. The organic phase is dried over sodium sulphate, in the course of which crystals precipitate out, which go into solution again with addition of a little methanol. The sodium sulphate is filtered off with suction and the mother liquor is concentrated in a rotary evaporator. The residue (crystals) is stirred in CH₂Cl₂ and filtered off with suction.

Yield (36%)

$R_f$=0.27 (dichloromethane:methanol, 20:1)

M.p.=160° C.

In analogy to the procedure of Example 55, the compounds shown in Table 4 are prepared:

TABLE 4

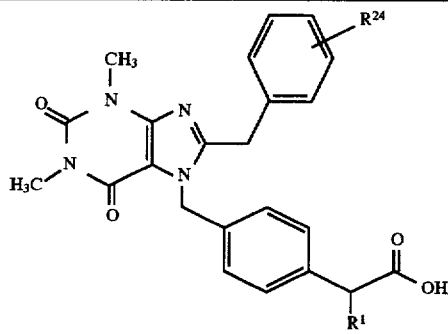

| Ex. No. | R¹ | R²⁴ | R_f* | M.p. (°C.) | Mass spectrum | Yield (% of theory) | Starting compound |
|---|---|---|---|---|---|---|---|
| 56 | (R&S) cPent | 2-OH | 0.31 (K) | (Foam) | 503(100%) | 29 | 40 |
| 57 | (R&S) cPent | 4-OH | 0.16 (K) | 100 (Foam) | 503(100%) | 73 | 42 |

Example 58

2-(R&S)-Cyclopentyl-[4-(1,3-dimethyl-2,6-dioxo-8-(4-methyl)phenyl-1,2,3,6-tetrahydro-purin-7-ylmethyl)phenyl] acetic acid hydrochloride

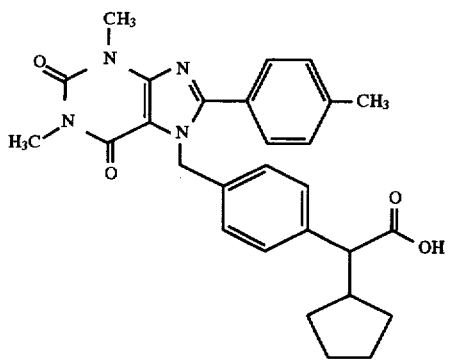

8.3 g (15.3 mmol) of the compound from Example 1 were dissolved in dioxane (60 ml), treated with concentrated hydrochloric acid and heated under reflux for 4 h. The mixture was cooled and treated with cold water. It was subsequently stirred for 20 minutes, and the crystals obtained were filtered off with suction.

Yield 7.21 g (97%);

M.p.>240° C.;

Rf=0.23 (dichloromethane:methanol, 20:1);

Mass (calculated for $C_{28}H_{30}N_4O_4$=486.58, mass spectrum (FAB, rel. intensity) 487 (100%);

$^1$H NMR (300 MHz, CDCl$_3$) δ7.45 (d, J=8.19 Hz, 2 H), 7.28–7.23 (m, 4 H), 6.98 (d, J=8.18 Hz, 2 H), 5.60 (s, 2 H), 3.64 (s, 3 H), 3.40 (s, 3 H), 3.23 (d, J=11.08 Hz, 1 H), 2.41 (m, 1 H), 2.40 (s, 3 H), 1.92 (m, 1 H), 1.70–1.20 (m, 6 H), 0.97 (m, 1 H).

The compounds shown in Tables 5, 6 and 7 are prepared in analogy to the procedure of Example 58:

TABLE 5

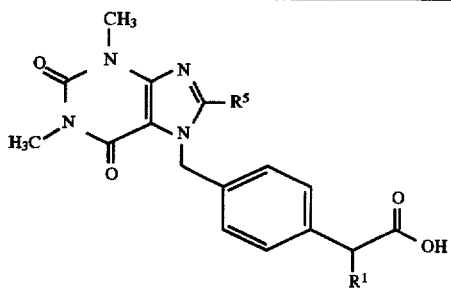

| Ex. No. | R¹ | R²⁴ | R_f* | M.p. (°C.) | Mass spectrum | Yield (% of theory) | Starting compound |
|---|---|---|---|---|---|---|---|
| 59 | (R&S) cPent | H | 0.27 (K) | 94 (Foam) | *397(40%) | 76 | 2 |
| 60 | (R&S) | Br | 0.35 (K) | 192 | | 82 | 3 |

TABLE 5-continued

| Ex. No. | R¹ | R²⁴ | R_f* | M.p. (°C.) | Mass spectrum | Yield (% of theory) | Starting compound |
|---|---|---|---|---|---|---|---|
| 61 | (R&S) cPent | CH₃ | 0.22 (K) | >230 | 411(100%) | 100 | 4 |
| 62 | (R&S) cPent | C₂H₅ | 0.20 (K) | 197 | 425(100%) | 64 | 5 |
| 63 | (R&S) cPent | cPro | 0.29 (K) | 94 | 437(100%) | 100 | 6 |
| 64 | (R&S) cPent | cPent | 0.47 (K) | 96 (Foam) | 465(100%) | 83 | 7 |
| 65 | (R&S) cPent | —CH₂-cHex | 0.38 (K) | 217 | *493(100%) | 74 | 8 |
| 66 | (R&S) cPent | (ethyl-thiophene) | 0.31 (K) | 190 | 493(100%) | 41 | 9 |
| 67 | (R&S) cPent | (phenyl) | 0.39 (J) | | | 100 | 10 |
| 68 | (R&S) cPent | (2-CH₃-phenyl) | 0.28 (K) | 185 | 487(100%) | 100 | 11 |
| 69 | (R&S) cPent | (4-CH₃-phenyl) | 0.24 (K) | 155 | 487(100%) | 84 | 12 |
| 70 | (R&S) cPent | (2,5-diCH₃-phenyl) | 0.35 (K) | 165 | 501(100%) | 96 | 13 |
| 71 | (R&S) cPent | (4-Ph-phenyl) | 0.36 (K) | 218 | 549(100%) | 56 | 14 |
| 72 | (R&S) cPent | (4-Cl-phenyl) | 0.33 (K) | 130 (Foam) | 507(100%) | 67 | 15 |
| 73 | (R&S) cPent | (4-CF₃-phenyl) | 0.31 (K) | 132 | 541(80%) 149(100%) | 85 | 16 |

TABLE 5-continued

| Ex. No. | R¹ | R²⁴ | R_f* | M.p. (°C.) | Mass spectrum | Yield (% of theory) | Starting compound |
|---|---|---|---|---|---|---|---|
| 74 | (R&S) cPent | 4-OCH₃-phenyl | 0.35 (K) | 122 (Foam) | 503(100%) | 88 | 17 |
| 75 | (R&S) cPent | 4-N(CH₃)₂-phenyl | 0.29 (K) | >245 | *516(70%) 307(100%) | 88 | 18 |
| 76 | (R&S) cPent | 4-N(C₂H₅)₂-phenyl | 0.46 (K) | (Foam) | 544(100%) | 100 | 19 |
| 77 | (R&S) cPent | 2-pyridyl | 0.23 (K) | >240 | 474(100%) | 83 | 20 |
| 78 | (R&S) cPent | 3-pyridyl | 0.52 (L) | — | 474(100%) | 27 | 21 |
| 79 | (R&S) cPent | 4-pyridyl | 0.25 (L) | >240 | 474(100%) | 72 | 22 |
| 80 | (R&S) cPent | 3-thienyl | 0.23 (K) | 217 | 479(100%) | 66 | 23 |
| 81 | (R&S) cPent | 2-thienyl | 0.34 (K) | 215–16 | 479(100%) | 45 | 24 |
| 82 | (R&S) cPent | 3-methyl-2-thienyl | 0.32 (K) | >235 | 493(100%) | 100 | 25 |
| 83 | (R&S) cPent | 5-methyl-2-thienyl | 0.23 (K) | 112 (Foam) | 493(100%) | 81 | 26 |
| 84 | (R&S) cPent | 3-bromo-5-methyl-2-thienyl | 0.35 (K) | >235 | 557(100%) | 100 | 27 |

TABLE 5-continued

| Ex. No. | R¹ | R²⁴ | $R_f$* | M.p. (°C.) | Mass spectrum | Yield (% of theory) | Starting compound |
|---|---|---|---|---|---|---|---|
| 85 | (R&S) cPent | —CH=CH—(phenyl) | 0.35 (K) | >240 | 476(50%) | | 28 |

TABLE 6

| Ex. No. | R¹ | R²⁵ | $R_f$* | M.p. (°C.) | Mass spectrum | Yield (% of theory) | Starting compound |
|---|---|---|---|---|---|---|---|
| 86 | (R&S) cPent | H | 0.44 (K) | 97 | 487(100%) | 90 | 29 |
| 87 | (R&S) cHex | H | 0.29 (K) | 117 (Foam) | 501(100%) | 55 | 30 |
| 88 | (R&S) cHept | H | 0.41 (K) | 214 | *514(100%) | 60 | 31 |
| 89 | (R&S)Ph | H | 0.22 (K) | 130 | 495(100%) | 42 | 32 |
| 90 | (R&S) cPent | 2-CH₃ | 0.42 (K) | 192 | 501(100%) | 94 | 33 |
| 91 | (R&S) cPent | 3-CH₃ | 0.24 (K) | 196 | 501(100%) | 91 | 34 |
| 92 | (R&S) cPent | 4-CH₃ | 0.27 (K) | 222 | 501(100%) | 97 | 35 |
| 93 | (R&S) cPent | 4-Ph | 0.13 (K) | 215 | 563(100%) | 100 | 36 |
| 94 | (R&S) cPent | 2-Cl | 0.34 (K) | 155 | 521(100%) | 100 | 37 |
| 95 | (R&S) cPent | 3-Cl | 0.25 (K) | 194 | 521(100%) | 68 | 38 |
| 96 | (R&S) cPent | 4-F | 0.25 (K) | 213 | 505(100%) | 94 | 39 |
| 97 | (R&S) cPent | 2-OCH₃ | 0.28 (K) | 63 | 517(100%) | 100 | 40 |
| 98 | (R&S) cPent | 3-OCH₃ | 0.22 (K) | 188 | 517(100%) | 64 | 41 |
| 99 | (R&S) cPent | 4-OCH₃ | 0.26 (K) | 210 | 517(100%) | 92 | 42 |

TABLE 7

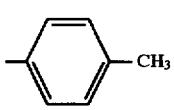

| Ex. No. | R¹ | R³ | R⁴ | R⁵ | T | V | R_f* | M.p. (°C.) | Mass spectrum | Yield (% of theory) | Starting compound |
|---|---|---|---|---|---|---|---|---|---|---|---|
| 100 | (R&S) cPent | $C_2H_5$ | $C_2H_5$ | H | O | O | 0.27 (K) | 110 | 425 (100%) | 100 | 43 |
| 101 | (R&S) cPent | $C_2H_5$ | $C_2H_5$ | $CH_3$ | O | O | 0.24 (K) | 82–85 | 439 (100%) | 100 | 44 |
| 102 | (R&S) cPent | $C_2H_5$ | $C_2H_5$ | $C_2H_5$ | O | O | 0.20 (K) | 181 | 453 (100%) | 96 | 45 |
| 103 | (R&S) cPent | $C_2H_5$ | $C_2H_5$ | cPro | O | O | 0.30 (K) | 98 (Foam) | 465 (100%) | 78 | 46 |
| 104 | (R&S) cPent | $C_2H_5$ | $C_2H_5$ | Ph | O | O | 0.38 (K) | 100 (Foam) | 501 (100%) | 80 | 47 |
| 105 | (R&S) cPent | $C_2H_5$ | $C_2H_5$ | 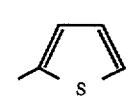 | O | O | 0.16 (K) | 92 (Foam) | 515 (100%) | 75 | 48 |
| 106 | (R&S) cPent | $C_2H_5$ | $C_2H_5$ | 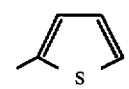 | O | O | 0.33 (K) | 232 | 507 (80%) 464 (100%) | 85 | 49 |
| 107 | (R&S) cPent | $CH_3$ | iBu | H | O | O | 0.33 (K) | 76 (Foam) | 439 (100%) | 98 | 50 |
| 108 | (R&S) cPent | $CH_3$ | $CH_3$ | $CH_3$ | S | O | 0.12 (J) | 222 | 427 (100%) | 100 | 51 |
| 109 | (R&S) cPent | $CH_3$ | $CH_3$ | $C_2H_5$ | S | O | 0.14 (J) | 172 | 441 (100%) | 100 | 52 |
| 110 | (R&S) cPent | $CH_3$ | $CH_3$ | 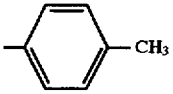 | S | O | 0.15 (J) | >235 | 495 (100%) | 100 | 53 |
| 111 | (R&S) cPent | $CH_3$ | $CH_3$ | 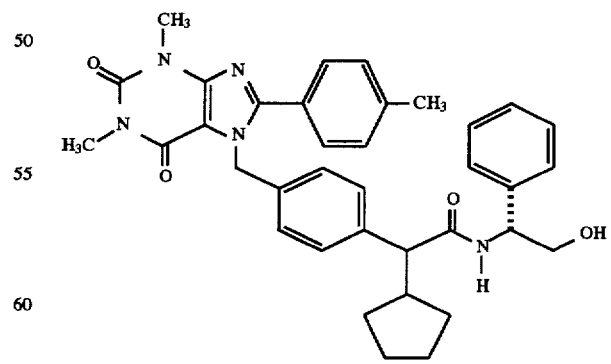 | S | O | 0.26 (J) | >235 | 503 (40%) 55 (100%) | 86 | 54 |

Example 112

N-[2-(R)-Phenyl-1-hydroxyethane]-2-(R&S)-cyclopentyl-[4-(1,3-dimethyl)-2,6-dioxo-8-(4-methyl)phenyl-1,2,3,6-tetrahydro-purin-7-ylmethyl)phenyl]acetamide

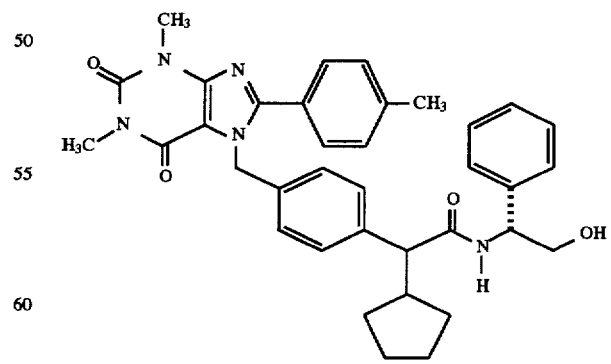

6.1 g (12.5 mmol) of the compound from Example 58, (R)-phenylglycinol (1.71 g, 12.5 mmol), 1-hydroxy-1-benzotriazole (1.86 g, 13.8 mmol), N'-(3-dimethylaminopropyl)-N-ethylcarbodiimide hydrochloride(2.76 g, 14.4 mmol) and triethylamine (2.53 g, 25 mmol) are dissolved successively in CH$_2$Cl$_2$ and stirred overnight at room temperature. A further 15 ml of CH$_2$Cl$_2$ are added and the mixture is washed with aqueous NH$_4$Cl and NaHCO$_3$ solution and with water. The organic phase is dried over sodium sulphate and evaporated. The residue is purified by column chromatography.

Yield 6.59 g (87%);

M.p. 87° C. (foam);

R$_f$=0.32 (dichloromethane:methanol, 20:1);

Mass (calculated) for C$_{36}$H$_{39}$N$_5$O$_4$=605.75, mass spectrum (FAB, rel. intensity) 606 (100%), 105 (95%).

The compounds shown in Tables 8, 9 and 10 are prepared in analogy to the procedure of Example 112. The compounds are either obtained directly as pure diastereomers, or they are separated by column chromatography according to customary methods starting from the racemate.

TABLE 8

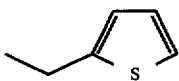

| Ex. No. | R$^1$ | R$^5$ | R$_f$* | M.p. (°C.) | Mass spectrum | Yield (% of theory) | Starting compound |
|---|---|---|---|---|---|---|---|
| 113 | (R&S) cPent | H | 0.27 (K) | 96 (Foam) | 516 (100%) | 70 | 59 |
| 114 | (dia A) cPent | H | 0.27 (K) | (Foam) | | | 113 |
| 115 | (dia B) cPent | H | 0.25 (K) | 162–163 | | | 113 |
| 116 | (R&S) cPent | Br | 0.33 (K) | 109 (Foam) | 596 (35%) 171 (100%) | 88 | 60 |
| 117 | (dia A) cPent | Br | | 183–185 | 596 (35%) 572 (100%) | | 116 |
| 118 | (dia B) cPent | Br | | 118–23 | 596 (35%) 550 (100%) | | 116 |
| 119 | (R&S) cPent | CH$_3$ | 0.35 (K) | 126–28 | 530 (60%) 105 (100%) | 85 | 61 |
| 120 | (R&S) cPent | C$_2$H$_5$ | 0.27 (K) | 105 (Foam) | 544 (100%) | 72 | 62 |
| 121 | (R&S) cPent | cPro | 0.36 (K) | 110 (Foam) | 556 (80%) 105 (100%) | 73 | 63 |
| 122 | (R&S) cPent | cPent | 0.33 (K) | 194 | 584 (100%) | 65 | 64 |
| 123 | (R&S) cPent | —CH$_2$cHex | 0.31 (K) | 117 (Foam) | 612 (100%) | 69 | 65 |
| 124 | (dia A) cPent | —CH$_2$cHex | 0.46 (K) | 173 | C, HN Pent | | 123 |
| 125 | (dia B) cPent | —CH$_2$cHex | 0.46 (K) | 90 (Foam) | 612 (100%) | | 123 |
| 126 | (R&S) cPent | 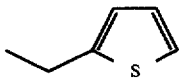 | 0.35 (K) | 112 (Foam) | 612 (100%) | 81 | 66 |
| 127 | (dia A) cPent | 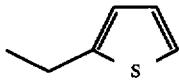 | 0.16 (K) | 183 | 612 (50%) 227 (100%) | | 126 |
| 128 | (dia B) cPent |  | 0.16 (K) | 82 (Foam) | 612 (40%) 105 (100%) | | 126 |
| 129 | (R&S) cPent | 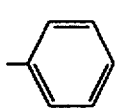 | 0.50 (L) | | | 98 | 67 |
| 130 | (dia A) cPent | 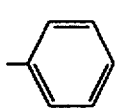 | 0.50 (L) | | 592 (100%) | | 129 |

TABLE 8-continued

| Ex. No. | R¹ | R⁵ | R_f* | M.p. (°C.) | Mass spectrum | Yield (% of theory) | Starting compound |
|---|---|---|---|---|---|---|---|
| 131 | (dia B) cPent | phenyl | 0.50 (L) | | 592 (100%) | | 129 |
| 132 | (R&S) cPent | 2-CH₃-phenyl | 0.31 (K) | 128 (Foam) | 606 (100%) | 79 | 68 |
| 133 | (R&S) cPent | 3-CH₃-phenyl | 0.25 (K) | 115 (Foam) | 606 (100%) | 81 | 69 |
| 134 | (dia A) cPent | 3-CH₃-phenyl | 0.23 (K) | 189–91 | 606 (50%) 171 (100%) | | 133 |
| 135 | (dia B) cPent | 3-CH₃-phenyl | 0.25 (K) | 154 | 606 (100%) | | 133 |
| 136 | (dia A) cPent | 4-CH₃-phenyl | 0.46 (K) | 104 (Foam) | | | 112 |
| 137 | (dia B) cPent | 4-CH₃-phenyl | 0.46 (K) | 198 (Foam) | | | 112 |
| 138 | (R&S) cPent | 2,4-(CH₃)₂-phenyl | 0.25 (K) | 132 (Foam) | 620 (100%) | 85 | 70 |
| 139 | (R&S) cPent | 4-Ph-phenyl | 0.28 (K) | 105 (Foam) | 668 (70%) 154 (100%) | 86 | 71 |
| 140 | (R&S) cPent | 4-Cl-phenyl | 0.34 (K) | 132 (Foam) | 626 (100%) | 85 | 72 |

TABLE 8-continued

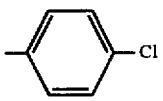

| Ex. No. | R¹ | R⁵ | R_f* | M.p. (°C.) | Mass spectrum | Yield (% of theory) | Starting compound |
|---|---|---|---|---|---|---|---|
| 141 | (dia A) cPent | 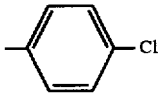 4-Cl-phenyl | 0.45 (K) | 80 (Foam) | | | 140 |
| 142 | (dia B) cPent | 4-Cl-phenyl | 0.45 (K) | 198 | | | 140 |
| 143 | (R&S) cPent | 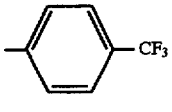 4-CF₃-phenyl | 0.34 (K) | 130 (Foam) | 660 (100%) | 69 | 73 |
| 144 | (dia A) cPent | 4-CF₃-phenyl | 0.47 (K) | 245 | 660 (50%) 171 (100%) | | 143 |
| 145 | (dia B) cPent | 4-CF₃-phenyl | 0.45 (K) | 212 | C, H, N Anal. | | 143 |
| 146 | (R&S) cPent | 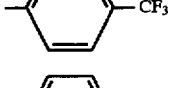 4-OCH₃-phenyl | 0.20 (K) | 126 (Foam) | 622 (100%) | 84 | 74 |
| 147 | (dia A) cPent | 4-OCH₃-phenyl | 0.43 (K) | O1 | 622 (351) 105 (100%) | | 146 |
| 148 | (dia B) cPent | 4-OCH₃-phenyl | 0.45 (K) | 201 | C, H, N Anal. | | 146 |
| 149 | (R&S) cPent | 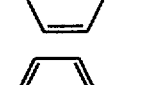 4-N(CH₃)₂-phenyl | 0.25 (K) | 140 (Foam) | 635 (100%) | 13 | 75 |
| 150 | (R&S) cPent | 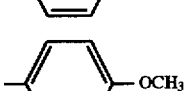 4-N(C₂H₅)₂-phenyl | 0.24 (K) | 128 (Foam) | 663 (100%) | 72 | 76 |
| 151 | (R&S) cPent | 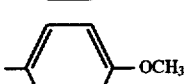 2-pyridyl | 0.28 (K) | >240 | 593 (100%) | 64 | 77 |
| 152 | (R&S) cPent | 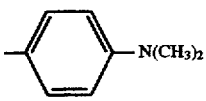 3-pyridyl | 0.14 (K) | 123 (Foam) | 593 (100%) | 81 | 78 |

TABLE 8-continued

| Ex. No. | R¹ | R⁵ | R_f* | M.p. (°C.) | Mass spectrum | Yield (% of theory) | Starting compound |
|---|---|---|---|---|---|---|---|
| 153 | (R&S) cPent | 4-pyridyl | | | | | 79 |
| 154 | (R&S) cPent | 3-thienyl | 0.21 (K) | 115 (Foam) | 598 (60%) 105 (100%) | 82 | 80 |
| 155 | (dia A) cPent | 3-thienyl | 0.43 (K) | 174–76 | 598 (100%) | | 154 |
| 156 | (dia B) cPent | 3-thienyl | 0.49 (K) | 197–99 | 598 (100%) | | 154 |
| 157 | (R&S) cPent | 2-thienyl | 0.30 (K) | (Foam) | 598(30%) 307 (100%) | 49 | 81 |
| 158 | (dia A) cPent | 2-thienyl | 0.34 (K) | 136 | | | 157 |
| 159 | (dia B) cPent | 2-thienyl | 0.31 (K) | 128 | | | 157 |
| 160 | (R&S) cPent | 3-methyl-2-thienyl (H₃C) | 0.46 (K) | 155 | 612 (100%) | 60 | 82 |
| 161 | (dia A) cPent | 3-methyl-2-thienyl (H₃C) | 0.41 (K) | 123 | 612 (100%) | | 160 |
| 162 | (dia B) cPent | 3-methyl-2-thienyl (H₃C) | 0.37 (K) | 187 | C, H, N Anal. | | 160 |
| 163 | (R&S) cPent | 5-methyl-2-thienyl | 0.39 (J) | 97 (Foam) | 612 (60%) 57 (100%) | 85 | 83 |
| 164 | (R&S) cPent | 4-bromo-5-methyl-2-thienyl | 0.48 (K) | >235 | 676(20%) 55 (100%) | 61 | 84 |

TABLE 8-continued

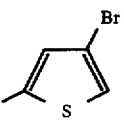

| Ex. No. | R¹ | R⁵ | $R_f$* | M.p. (°C.) | Mass spectrum | Yield (% of theory) | Starting compound |
|---|---|---|---|---|---|---|---|
| 165 | (dia A) cPent | ![thiophene-Br] | 0.37 (K) | 175 | C, H, N Anal. | | 164 |
| 166 | (dia B) cPent | ![thiophene-Br] | 0.37 (K) | 169 | 676 (100%) | | 164 |
| 167 | (R&S) cPent | —CH=CH—⟨phenyl⟩— | 0.49 (K) | 160–69 | 618 (100%) | 31 | 85 |

TABLE 9

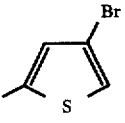

| Ex. No. | R¹ | R²⁶ | $R_f$* | M.p. (°C.) | Mass spectrum | Yield (% of theory) | Starting compound |
|---|---|---|---|---|---|---|---|
| 168 | (R&S)cPent | H | 0.22 (K) | (Foam) | 606(100%) | 98 | 86 |
| 169 | (dia A)cPent | H | | 204–7 | | | 168 |
| 170 | (dia B)cPent | H | | (Foam) | | | 168 |
| 171 | (R&S)cHex | H | 0.40 (K) | | 620(100%) | 86 | 87 |
| 172 | (dia A)cHex | H | 0.33 (K) | 226 | C, H, N Anal. | | 171 |
| 173 | (dia B)cHex | H | 0.34 (K) | 116 | 620(45%) 185(100%) | | 171 |
| 174 | (R&S)cHept | H | 0.36 (K) | 108 (Foam) | | 92 | 88 |
| 175 | (dia A)cHept | H | | 202 | | | 174 |
| 176 | (dia B)cHept | H | | 100 (Foam) | | | 174 |
| 177 | (R&S)Ph | H | 0.15 (K) | 106–10 | 614(100%) | 50% | 89 |
| 178 | (R&S)cPent | 2-CH₃ | 0.38 (K) | 137 | 620(100%) | 54 | 90 |
| 179 | (R&S)cPent | 3-CH₃ | 0.28 (K) | 121 (Foam) | 620(100%) | 36 | 91 |
| 180 | (dia A)cPent | 3-CH₃ | 0.16 (K) | 200 | C, H, N Anal. | | 179 |
| 181 | (dia B)cPent | 3-CH₃ | 0.17 (K) | 166 | | | 179 |
| 182 | (R&S)cPent | 4-CH₃ | 0.33 (K) | 113 (Foam) | 620(100%) | 92 | 92 |

TABLE 9-continued

| Ex. No. | R¹ | R²⁶ | $R_f$* | M.p. (°C.) | Mass spectrum | Yield (% of theory) | Starting compound |
|---|---|---|---|---|---|---|---|
| 183 | (dia A)cPent | 4-CH₃ | 0.37 (K) | 223 | C, H, N Anal. | | 182 |
| 184 | (dia B)cPent | 4-CH₃ | 0.40 (K) | 208 | C, H, N Anal. | | 182 |
| 185 | (R&S)cPent | 4-Phenyl | 0.49 (K) | 180 | 682(100%) | 47 | 93 |
| 186 | (dia A)cPent | 4-Phenyl | 0.32 (K) | >230 | C, H, N Anal. | | 185 |
| 187 | (dia B)cPent | 4-Phenyl | 0.31 (K) | 200 | C, H, N Anal. | | 185 |
| 188 | (R&S)cPent | 2-Cl | 0.39 (K) | 113 (Foam) | 640(100%) | 77 | 94 |
| 189 | (dia A)cPent | 2-Cl | 0.38 (K) | 208 | C, H, N Anal. | | 188 |
| 190 | (dia B)cPent | 2-Cl | 0.34 (K) | 142 | C, H, N Anal. | | 188 |
| 191 | (R&S)cPent | 3-Cl | 0.41 (K) | 142 | 640(100%) | 86 | 95 |
| 192 | (dia A)cPent | 3-Cl | 0.35 (K) | 200 | C, H, N Anal. | | 191 |
| 193 | (dia B)cPent | 3-Cl | 0.35 (K) | 183 | | | 191 |
| 194 | (R&S)cPent | 4-F | 0.42 (K) | 151 (Foam) | 624(100%) | 81 | 96 |
| 195 | (dia A)cPent | 4-F | 0.38 (K) | 212 | C, H, N Anal. | | 194 |
| 196 | (dia B)cPent | 4-F | 0.37 (K) | 189 | C, H, N Anal. | | 194 |
| 197 | (R&S)cPent | 2-OCH₃ | 0.37 (K) | 120 (Foam) | 636(100%) | 61 | 97 |
| 198 | (R&S)cPent | 3-OCH₃ | 0.48 (K) | 105 (Foam) | 636(100%) | 79 | 98 |
| 199 | (dia A)cPent | 3-OCH₃ | 0.19 (K) | 188 | | | 198 |
| 200 | (dia B)cPent | 3-OCH₃ | 0.15 (K) | 178 | | | 198 |
| 201 | (R&S)cPent | 4-OCH₃ | 0.35 (K) | 110 (Foam) | 636(100%) | 70 | 99 |
| 202 | (dia A)cPent | 4-OCH₃ | 0.29 (K) | | | | 201 |
| 203 | (dia B)cPent | 4-OCH₃ | 0.28 (K) | | | | 201 |
| 204 | (R&S)cPent | 2-OH | 0.23 (K) | 130 | 622(100%) | 67 | 56 |
| 205 | (dia A)cPent | 2-OH | 0.26 (K) | 01 | 622(40%) 105(100%) | | 204 |
| 206 | (dia B)cPent | 2-OH | 0.26 (K) | 01 | 622(50%) 105(100%) | | 204 |
| 207 | (R&S)cPent | 3-OH | 0.14 (K) | 128 (Foam) | 622(100%) | 70 | 55 |
| 208 | (dia A)cPent | 3-OH | 0.38 (K) | 143 | 622(100%) | | 207 |
| 209 | (dia B)cPent | 3-OH | 0.38 (K) | 145 | 622(100%) | | 207 |
| 210 | (R&S)cPent | 4-OH | | | | | 57 |

TABLE 10

| Ex. No. | R¹ | R³ | R⁴ | R⁵ | R¹⁴ | R¹⁵ | T | V | $R_f$* | M.p. (°C.) | Mass spectrum | Yield (% of theory) | Starting compound |
|---|---|---|---|---|---|---|---|---|---|---|---|---|---|
| 211 | (R&S) cPent | C₂H₅ | C₂H₅ | H | (R)Ph | CH₂OH | O | O | 0.40 (J) | | 544(100%) | 67 | 100 |
| 212 | (dia A) cPent | C₂H₅ | C₂H₅ | H | (R)Ph | CH₂OH | O | O | 0.40 (J) | 110 | | | 211 |
| 213 | (dia B) cPent | C₂H₅ | C₂H₅ | H | (R)Ph | CH₂OH | O | O | 0.35 (J) | 121 | | | 211 |
| 214 | (R&S) cPent | C₂H₅ | C₂H₅ | CH₃ | (R)Ph | CH₂OH | O | O | 0.48 (K) | 112–14 | 558(100%) | 83 | 101 |
| 215 | (R&S) cPent | C₂H₅ | C₂H₅ | C₂H₅ | (R)Ph | CH₂OH | O | O | 0.20 (J) | 104 | 572(80%) | 84 | 102 |
| 216 | (R&S) cPent | C₂H₅ | C₂H₅ | cPro | (R)Ph | CH₂OH | O | O | 0.36 (K) | 104 (Foam) | 584(100%) | 87 | 103 |
| 217 | (R&S) cPent | C₂H₅ | C₂H₅ | Ph | (R)Ph | CH₂OH | O | O | 0.31 (K) | 115 (Foam) | 620(100%) | 87 | 104 |
| 218 | (R&S) cPent | C₂H₅ | C₂H₅ | phenyl-CH₃ | (R)Ph | CH₂OH | O | O | 0.44 (K) | 168 | 634(90%) 105(100%) | 90 | 105 |
| 219 | (R&S) cPent | C₂H₅ | C₂H₅ | thienyl | (R)Ph | CH₂OH | O | O | 0.38 (K) | 115–17 (Foam) | 626(70%) 105(100%) | 90 | 106 |
| 220 | (R&S) cPent | CH₃ | iBu | H | (R)Ph | CH₂OH | O | O | 0.39 (K) | 101 (Foam) | 558(100%) | 79 | 107 |
| 221 | (dia A) cPent | CH₃ | iBu | H | (R)Ph | CH₂OH | O | O | 0.24 (K) | 134 | 558(100%) | | 220 |
| 222 | (dia B) cPent | CH₃ | iBu | H | (R)Ph | CH₂OH | O | O | 0.20 (K) | 186 | C, H, N Anal. | | 220 |
| 223 | (R&S) cPent | CH₃ | CH₃ | CH₃ | (R)Ph | CH₂OH | S | O | 0.45 (J) | 120 (Foam) | 546(90%) | 68 | 108 |
| 224 | (R&S) cPent | CH₃ | CH₃ | C₂H₅ | (R)Ph | CH₂OH | S | O | 0.45 (K) | 113 (Foam) | 560(100%) | 58 | 109 |
| 225 | (R&S) cPent | CH₃ | CH₃ | thienyl | (R)Ph | CH₂OH | S | O | 0.64 (J) | 130 (Foam) | 614(90%) 154(100%) | 46 | 110 |
| 226 | (R&S) cPent | CH₃ | CH₃ | -phenyl-CH₃ | (R)Ph | CH₂OH | S | O | 0.41 (J) | 104 (Foam) | 622(100%) | 79 | 111 |

Example 227

2-(R&S)-Cyclopentyl-2-[4-(1,3-dimethyl-2,6-dioxo-8-(2-phenyl-ethyl)-1,2,3,6-tetra-hydro-purin-7-yl-methyl) phenyl]acet-N-[1-(R)-1-phenyl-2-hydroxy-ethyl)amide 0.40 g (0.648 mmol) of the compound from Example 167 is dissolved in 10 ml of methanol and 10 ml of acetic acid. A spatula tipful of palladium-carbon (10% strength) is added to this solution and it is hydrogenated for 4 hours under normal pressure. The mixture is filtered off with suction through Celite and concentrated in a rotary evaporator. The residue is taken up in $CH_2Cl_2$ and water, adjusted to pH 8 with sodium hydrogen carbonate and extracted. The organic phase is dried over sodium sulphate and concentrated in a rotary evaporator. The residue is purified by column chromatography.

Yield: 0.180 g (44.9%)

$R_f$=0.16 (dichloromethane:methanol 20:1)

Mass (calculated) for $C_{37}H_{41}N_5O_4$=619.77

We claim:

1. Substituted xanthines of formula (I)

in which

A represents a radical of the formula in which

R$^3$, R$^4$, R$^6$ and R$^7$ are identical or different and denote hydrogen, cycloalkyl having 3 to 7 carbon atoms or aryl having 6 to 10 carbon atoms, or denote straight-chain or branched alkyl or alkenyl in each case having up to 8 carbon atoms, each of which is optionally substituted by halogen, hydroxyl or aryl having 6 to 10 carbon atoms, T, V, X and Y are identical or different and denote an oxygen or sulphur atom, R$^5$ and R$^8$ are identical or different and denote hydrogen, halogen, cycloalkyl having 3 to 8 carbon atoms or straight-chain or branched alkyl or alkenyl in each case having up to 8 carbon atoms, each of which is optionally substituted by 1) cycloalkyl having 3 to 8 carbon atoms, or by 2) a 5- to 6-membered, aromatic, optionally benzo-fused heterocycle having up to 3 heteroatoms from the series S, N and/or O, 3) or by aryl having 6 to 10 carbon atoms, where the cyclic substituents identified by 1), 2), and 3), can be substituted identically or differently up to 3 times by a 5- to 6-membered, aromatic heterocycle having up to 3 heteroatoms from the series S, N and/or O, or by phenyl, benzyl, halogen, hydroxyl, carboxyl or straight-chain or branched alkyl, alkoxy or alkoxycarbonyl in each case having up to 6 carbon atoms, or R$^5$ and R$^8$ denote aryl having 6 to 10 carbon atoms or a 5- to 7-membered aromatic, optionally benzo-fused heterocycle having up to 3 heteroatoms from the series S, N and/or O, each of which is optionally substituted identically or differently up to 3 times by halogen, phenyl, trifluoromethyl, hydroxy, carboxyl or straight-chain of branched alkyl, alkoxy or alkoxycarbonyl in each case having up to 6 carbon atoms or by a group of the formula —(CO)$_a$—NR$^9$R$^{10}$, in which a denotes a number 0 or 1, R$^9$ and R$^{10}$ are identical or different and denote hydrogen, phenyl or straight-chain or branched alkyl or acyl in each case having up to 5 carbon atoms, D and E are identical or different and represent hydrogen, halogen, trifluoromethyl, hydroxyl, carboxyl or straight-chain or branched alkyl, alkoxy or alkoxycarbonyl in each case having up to 6 carbon atoms, R$^1$ represents hydrogen or cycloalkyl having 3 to 8 carbon atoms, or represents straight-chain or branched alkyl or alkenyl in each case having up to 8 carbon atoms, each of which is optionally substituted by cycloalkyl having 3 to 6 carbon atoms, phenyl or a 5- to 6-membered aromatic heterocycle having up to 3 heteroatoms from the series S, N and/or O, or represents phenyl or a 5- to 6-membered aromatic heterocycle having up to 3 heteroatoms from the series S, N and/or O, where the ring systems are optionally substituted identically or differently up to 3 times by halogen, phenyl, trifluoromethyl or straight-chain or branched alkyl or alkoxy in each case having up to 5 carbon atoms, hydroxyl or a group of the formula —NR$^{11}$R$^{12}$, in which R$^{11}$ and R$^{12}$ have the meaning of R$^9$ and R$^{10}$ given above and are identical to or different from this, L represents an oxygen or sulphur atom, R$^2$ represents mercapto, hydroxyl, straight-chain or branched alkoxy having up to 8 carbon atoms or the group of the formula in which R$^{13}$ denotes hydrogen or straight-chain or branched alkyl having up to 4 carbon atoms, R$^{14}$ denotes hydrogen, phenyl or a 5- to 6-membered aromatic heterocycle having up to 3 heteroatoms from the series S, N and/or O, R$^{15}$ denotes hydrogen or straight-chain or branched alkyl having up to 8 carbon atoms, which is optionally substituted by hydroxyl, and their salts.

2. Substituted xanthines of the formula according to claim 1, in which

63

A represents a radical of the formula

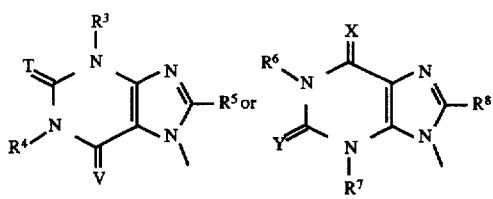

in which
R³, R⁴, R⁶ and R⁷ are identical or different and denote hydrogen, phenyl, cyclopropyl, cyclopentyl or cyclohexyl, or
denote straight-chain or branched alkyl or alkenyl in each case having up to 6 carbon atoms, each of which is optionally substituted by fluorine, chlorine, bromine, hydroxyl or phenyl, T, V, X and T are identical or different and denote an oxygen or sulphur atom, R⁵ and R⁸ are identical or different and denote hydrogen, fluorine, chlorine, bromine, cyclopropyl, cyclobutyl, cyclopentyl, cyclohexyl, cycloheptyl or straight-chain or branched alkyl or alkenyl in each case having up to 6 carbon atoms, each of which is optionally substituted by cyclopropyl, cyclopentyl, cyclohexyl, cycloheptyl, naphthyl, phenyl, pyridyl, thienyl or furyl, which can be substituted identically or differently up to 2 times by phenyl, benzyl, fluorine, chlorine, bromine, hydroxyl or straight or branched alkyl or alkoxy in each case having up to 4 carbon atoms, or denote phenyl, pyridyl, thienyl or furyl, each of which is optionally substituted identically or differently up to 2 times by fluorine, chlorine, bromine, phenyl, trifluoromethyl, hydroxyl or straight-chain or branched alkyl or alkoxy in each case having up to 4 carbon atoms or a group of the formula —(CO)$_a$—NR⁹R¹⁰, in which a denotes a number 0 or 1, R⁹ and R¹⁰ are identical or different and denote hydrogen, phenyl or straight-chain or branched alkyl or acyl in each case having up to 4 carbon atoms, D and E are identical or different and represent hydrogen, fluorine, chlorine, bromine, trifluoromethyl hydroxyl or straight-chain or branched alkyl or alkoxy in each case having up to 4 carbon atoms, R¹ represents hydrogen, cyclopropyl, cyclobutyl, cyclopentyl, cyclohexyl, cycloheptyl or straight-chain or branched alkyl or alkenyl in each case having up to 6 carbon atoms, each of which is optionally substituted by cyclopropyl, cyclopentyl, cyclohexyl, phenyl, pyridyl or thienyl, or represents phenyl, pyridyl, furyl or thienyl, each of which is optionally substituted identically or differently up to 2 times by fluorine, chlorine, bromine, phenyl, trifluoromethyl or straight-chain or branched alkyl or alkoxy in each case having up to 4 carbon atoms or a group of the formula —NR¹¹R¹², in which R¹¹ and R¹² have the meaning of R⁹ and R¹⁰ given above and are identical to or different from this, L represents an oxygen or sulphur atom, R² represents mercapto, hydroxyl, straight-chain or branched alkoxy having up to 6 carbon atoms or the group of the formula

64

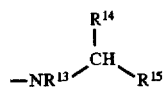

in which
R¹³ denotes hydrogen or straight-chain or branched alkyl having up to 4 carbon atoms, R¹⁴ denotes hydrogen, phenyl, pyridyl, furyl or thienyl, R¹⁵ denotes hydrogen or straight-chain or branched alkyl having up to 6 carbon atoms, which is optionally substituted by hydroxyl, and their salts.

3. Substituted xanthines of the formula according to claim 1, in which

A represents a radical of the formula

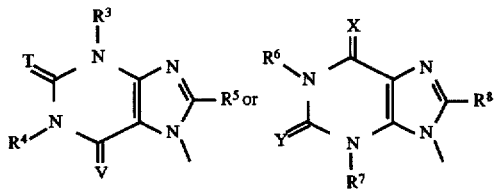

in which
R³, R⁴, R⁶ and R⁷ are identical or different and denote hydrogen, phenyl, cyclopropyl, cyclopentyl or cyclohexyl, or
denote straight-chain or branched alkyl or alkenyl in each case having up to 5 carbon atoms, each of which is optionally substituted by fluorine, chlorine, bromine, hydroxyl or phenyl, T, V, X and Y are identical or different and denote an oxygen or sulphur atom, R⁵ and R⁸ are identical or different and denote hydrogen, fluorine, chlorine, bromine, cyclopropyl, cyclobutyl, cyclopentyl, cyclohexyl, cycloheptyl or straight-chain or branched alkyl or alkenyl in each case having up to 5 carbon atoms, each of which is optionally substituted by cyclopropyl, cyclopentyl, cyclohexyl, cycloheptyl, phenyl, pyridyl, thienyl or furyl, which can be substituted identically or differently up to 2 times by phenyl, benzyl, fluorine, chlorine, bromine, hydroxyl or straight-chain or branched alkyl or alkoxy in each case having up to 3 carbon atoms, or denote phenyl, pyridyl, thienyl or furyl, each of which is optionally substituted identically or differently up to 2 times by fluorine, chlorine, bromine, phenyl, trifluoromethyl, hydroxyl or straight-chain or branched alkyl or alkoxy in each case having up to 3 carbon atoms or a group of the formula —(CO)$_a$—NR⁹R¹⁰, in which a denotes a number 0 or 1, R⁹ and R¹⁰ are identical or different and denote hydrogen, phenyl or straight-chain or branched alkyl or acyl in each case having up to 3 carbon atoms, D and E are identical or different and represent hydrogen, fluorine, chlorine, bromine or trifluoromethyl, R¹ represents hydrogen, cyclopropyl, cyclobutyl, cyclopentyl, cyclohexyl, cycloheptyl or straight-chain or branched alkyl or alkenyl in each case having up to 5 carbon atoms, each of which is optionally substituted by cyclopropyl, cyclopentyl, cyclohexyl, phenyl, pyridyl or thienyl, or represents phenyl, pyridyl, furyl or thienyl, each of which is optionally substituted identically or differently up to 2 times by fluorine, chlorine, bromine, phenyl, trifluoromethyl or straight-chain or branched alkyl or alkoxy in each case having up to 3 carbon atoms or a group of the formula —NR$^{11}$R$^{12}$, in which R$^{11}$ and R$^{12}$ have the meaning of R$^9$ and R$^{10}$ given above and are identical to or different from this, L represents an oxygen or sulphur atom, R$^2$ represents mercapto, hydroxyl, straight-chain or branched alkoxy having up to 5 carbon atoms or the group of the formula

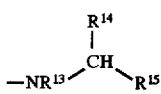

in which

R$^{13}$ denotes hydrogen or straight-chain or branched alkyl having up to 3 carbon atoms, R$^{14}$ denotes hydrogen, phenyl, pyridyl or thienyl, R$^{15}$ denotes hydrogen or straight-chain or branched alkyl having up to 3 carbon atoms, which is optionally substituted by hydroxyl, and their salts.

4. Substituted xanthines of the formula according to claim 1, in which

A represents a radical of the formula

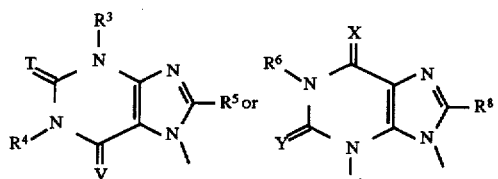

in which

R$^3$, R$^4$, R$^6$ and R$^7$ are hydrogen, straight-chain or branched alkyl in each case having up to 4 carbon atoms, T, V, X and Y are identical or different and denote an oxygen or sulphur atom, R$^5$ and R$^8$ are identical or different and denote hydrogen, fluorine, chlorine, bromine, cyclopropyl, cyclopentyl, cyclohexyl or straight-chain or branched alkyl or alkenyl in each case having up to 3 carbon atoms, each of which is optionally substituted by cyclopropyl, cyclopentyl, cyclohexyl, phenyl, pyridyl, thienyl or furyl, which can be substituted identically or differently up to 2 times by phenyl, benzyl, fluorine, chlorine, bromine, hydroxyl or straight-chain or branched alkyl or alkoxy in each case having up to 3 carbon atoms, or denote phenyl, pyridyl, thienyl or furyl, each of which is optionally substituted identically or differently up to 2 times by fluorine, chlorine, bromine, phenyl, trifluoromethyl, hydroxyl or straight-chain or branched alkyl or alkoxy in each case having up to 3 carbon atoms or a group of the formula —(CO)$_a$—NR$^9$R$^{10}$, in which a denotes the number 0, R$^9$ and R$^{10}$ are identical or different and denote hydrogen or straight-chain or branched alkyl in each case having up to 3 carbon atoms, D and E are identical or different and represent hydrogen, fluorine, chlorine, bromine or trifluoromethyl.

R$^1$ represents hydrogen, cyclopropyl, cyclopentyl, cyclohexyl, cycloheptyl, phenyl or straight-chain or branched alkyl having up to 5 carbon atoms, L represents an oxygen atom, R$^2$ represents hydroxyl, straight-chain or branched alkoxy having up to 5 carbon atoms or the group of the formula

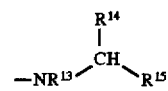

in which

R$^{13}$ denotes hydrogen or straight-chain or branched alkyl having up to 3 carbon atoms, R$^{14}$ denotes phenyl, R$^{15}$ denotes straight-chain or branched alkyl having up to 3 carbon atoms, which is optionally substituted by hydroxyl, and their salts.

5. Substituted xanthines according to claim 1 wherein such compound is N-[2-(R)-Phenyl-1-hydroxyethane]-2-(R)-cyclopentyl-[4-(1,3-dimethyl)-2,6-dioxo-8-benzyl-1,2,3,6-tetrahydro-purin-7-ylmethyl)phenyl]acetamide of the formula

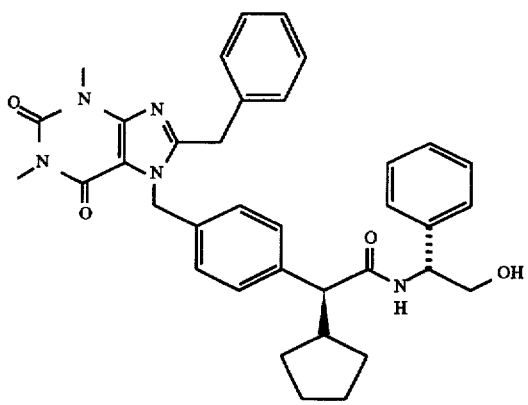

and salts thereof.

6. Substituted xanthines according to claim 1 wherein such compound is N-[2-(R)-Phenyl-1-hydroxyethane]-2-(R)-cyclopentyl-[4-(1,3-dimethyl)-2,6-dioxo-8-(4-methyl) phenyl-1,2,3,6-tetrahydro-purin-7-ylmethyl)phenyl] acetamide of the formula

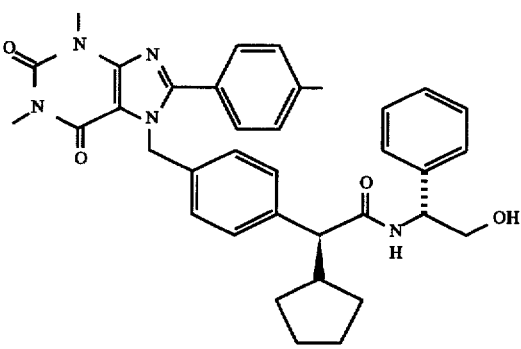

and salts thereof.

7. Substituted xanthines according to claim 1 wherein such compound is N-[2-(R)-Phenyl-1-hydroxyethane]-2-(R) cyclopentyl-[4-(1,3-dimethyl)-2,6-dioxo-8-(3-thienyl)-1,2, 3,6-tetrahydro-purin-7-ylmethyl)phenyl]acetamide of the formula

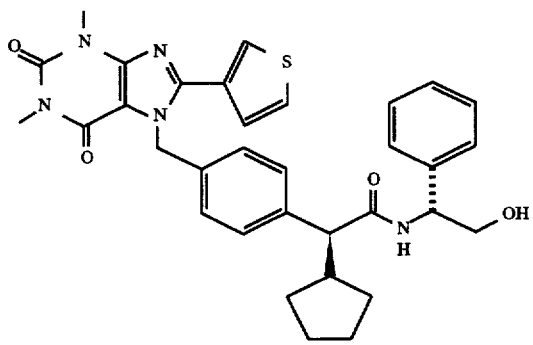

and salts thereof.

8. Substituted xanthines according to claim 1 wherein such compound is N-[2-(R)-Phenyl-1-hydroxyethane]-2-(R)-cyclopentyl-[4-(1,3-dimethyl)-2,6-dioxo-8-(2-thienyl)-1,2,3,6-tetrahydro-purin-7-ylmethyl)phenyl]acetamide of the formula

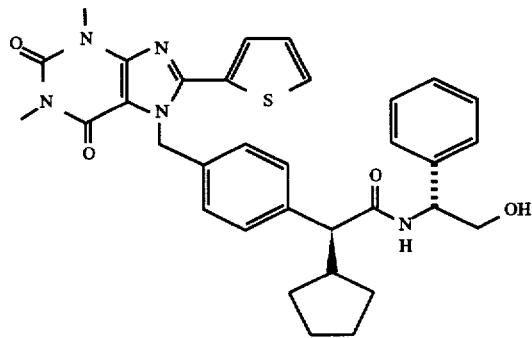

and salts thereof.

9. Substituted xanthines according to claim 1 wherein such compound is N-[2-(R)-Phenyl-1-hydroxyethane]-2-cyclopentyl-[4-(1,3-dimethyl)-2-thiooxo-6-oxo-8-ethyl-1,2,3,6-tetrahydro-purin-7-ylmethyl)phenyl]acetamide of the formula

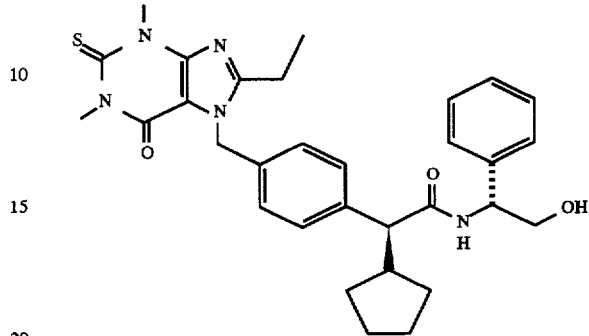

and salts thereof.

10. A composition for the treatment of atherosclerosis comprising an amount effective therefore of a compound or salt thereof according to claim 1 and a pharmacologically acceptable diluent.

11. The method of treating atherosclerosis in a patient in need thereof which comprises administering to such patient an amount effective therefore of a compound or salt thereof according to claim 1.

* * * * *

UNITED STATES PATENT AND TRADEMARK OFFICE
CERTIFICATE OF CORRECTION

PATENT NO. : 5,714,494
DATED : February 3, 1998
INVENTOR(S) : Connell, et al.

It is certified that error appears in the above-indentified patent and that said Letters Patent is hereby corrected as shown below:

Col. 63, line 20   Delete " T " (second occurrence) and substitute -- Y --

Signed and Sealed this

Ninth Day of February, 1999

Attest:

Attesting Officer

Acting Commissioner of Patents and Trademarks